(12) United States Patent
Vella

(10) Patent No.: US 11,083,769 B2
(45) Date of Patent: *Aug. 10, 2021

(54) WHOLE GREEN COFFEE BEAN PRODUCTS AND METHODS OF PRODUCTION AND USE FOR PREVENTING OR TREATING OBESITY AND DIABETES

(71) Applicant: GOBEAN GREEN COFFEE PRODUCTS, LLC, Chandler, AZ (US)

(72) Inventor: Thomas Vella, Scottsdale, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/149,412

(22) Filed: Oct. 2, 2018

(65) Prior Publication Data

US 2019/0054134 A1 Feb. 21, 2019

Related U.S. Application Data

(63) Continuation-in-part of application No. 14/716,869, filed on May 19, 2015, now Pat. No. 10,086,031, which is a continuation-in-part of application No. 13/215,174, filed on Aug. 22, 2011, now Pat. No. 9,034,410.

(51) Int. Cl.
| | |
|---|---|
| *A61K 36/74* | (2006.01) |
| *A23L 33/105* | (2016.01) |
| *A23F 5/08* | (2006.01) |
| *A23F 5/02* | (2006.01) |
| *A61K 9/48* | (2006.01) |

(52) U.S. Cl.
CPC ............... *A61K 36/74* (2013.01); *A23F 5/02* (2013.01); *A23F 5/08* (2013.01); *A23L 33/105* (2016.08); *A61K 9/4875* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 9,034,410 B2 * | 5/2015 | Vella | ......................... A23F 5/02 426/595 |
| 2010/0112098 A1 * | 5/2010 | Lemaire | ............... A61K 31/235 424/729 |

* cited by examiner

*Primary Examiner* — Susan Hoffman
(74) *Attorney, Agent, or Firm* — Allen F. Bennett; Bennett Intellectual Property

(57) ABSTRACT

Disclosed are novel processing methods for green coffee beans that result in novel green coffee bean products, including products that incorporate whole green coffee beans. Methods include selecting whole coffee beans in their fresh green unroasted state with naturally-occurring levels of phytonutrients, sterilizing and drying them, applying iterative grinding processes and stabilization techniques, all while avoiding high temperatures. Whole green coffee bean products created and defined by these methods are used to treat or prevent diabetes and obesity.

3 Claims, 15 Drawing Sheets

Fig. 7

TABLE 1: STUDY SCHEDULE OF EVENTS

| Event | Baseline/Screening/Week 0 | Week 6 | Week 12 |
|---|---|---|---|
| Informed Consent | Y | N | N |
| Health History | Y | N | N |
| Physical Exam | Y | N | N |
| Bodyweight/BMI, Caliper skin fold mid abdomen, % fat by BIA Impedance | Y | Y | Y |
| HR and BP | Y | Y | Y |
| EKG | Y | N | N |
| Anthropometrics | Y | Y | Y |
| Hunger & Satiety VAS | Y | Y | Y |
| Energy VAS | Y | Y | Y |
| Diet & Exercise Diaries | N | Y | Y |
| Blood Chemistries | Y | N | Y |
| Adverse Event Monitoring | N | Y | Y |
| Site Visits | Y | Y | Y |

Fig. 8

TABLE 2: STUDY SUBJECT FLOW CHART

| GOBEAN™ Study Protocol: 0595-G-0714 | |
|---|---|
| Date: | 8/8/2015 |
| Enrolled: | 74 |
| Baseline visit | 74 |
| Completed Week 6 | 51 |
| Completed Week 12 | 43 |
| Drop Outs | 31 |
| Screen Failures (DQ/PI) | 17 |
| Males | 26 |
| Females | 48 |

Fig. 9

TABLE 3A: DEMOGRAPHICS, BODY MEASUREMENTS AND VITALS (Baseline)

| Variable | Active (n=37) | Placebo (n=37) | p-value* |
|---|---|---|---|
| Gender, n (%) | | | 0.14 |
|   Males | 10 (27.0%) | 16 (43.2%) | |
|   Females | 27 (73.0%) | 21 (56.8%) | |
| Dropouts, n (%) | 15 (40.5%) | 16 (43.2%) | 0.81 |
| EKG – Normal, n (%) | 37 (100%) | 37 (100%) | --- |
| Age, years mean (SD), range | 44.8 (12.5) 18 to 65 | 43.4 (10.6) 24 to 63 | 0.60 |
| Baseline | Mean (SD) | Mean (SD) | |
| Height, in | 65.3 (4.2) | 66.0 (3.1) | 0.42 |
| Weight, lb. | 190.7 (31.0) | 190.5 (23.7) | 0.97 |
| BMI, kg/m$^2$ | 31.4 (3.1) | 30.6 (2.6) | 0.25 |
| Systolic blood pressure, mmHg | 124.0 (12.0) | 120.9 (9.1) | 0.22 |
| Diastolic blood pressure, mmHg | 79.5 (8.0) | 78.5 (7.2) | 0.57 |
| Pulse, beats/min | 76.1 (10.8) | 71.8 (10.0) | 0.08 |
| BIA scale % fat | 38.2 (7.8) | 35.3 (7.0) | 0.09 |
| Hip circumference, in. | 46.9 (3.0) | 45.5 (2.9) | 0.04 |
| Waist circumference, in. | 39.4 (3.8) | 39.7 (3.7) | 0.77 |
| Body Fat Caliper measurement, mm | 39.3 (11.3) | 38.8 (10.8) | 0.82 |

*Chi-square and independent samples t-test p-values

Fig. 10

TABLE 3B: DEMOGRAPHICS, BODY MEASUREMENTS AND VITALS (Week 6)

| Variable | Active (n=37) | Placebo (n=37) | p-value* |
|---|---|---|---|
| Week 6 | Mean (SD) | Mean (SD) | |
| Weight, lb. | 185.5 (28.4)² | 191.6 (20.5) | 0.39 |
| BMI, kg/m² | 31.2 (3.0) | 30.6 (2.6) | 0.45 |
| Systolic blood pressure, mmHg | 127.8 (16.3) | 126.4 (12.1) | 0.73 |
| Diastolic blood pressure, mmHg | 82.6 (8.4) | 79.4 (12.1) | 0.28 |
| Pulse, beats/min | 74.7 (11.6) | 69.2 (8.3) | 0.06 |
| BIA scale % fat | 39.7 (7.1) | 37.7 (7.3) | 0.33 |
| Hip circumference, in. | 46.4 (3.2) | 45.3 (4.2) | 0.30 |
| Waist circumference, in. | 39.2 (4.4) | 40.2 (3.7) | 0.38 |
| Body Fat Caliper measurement, mm | 43.6 (8.9) | 40.8 (9.5) | 0.30 |
| Week 6 Change from Baseline | Mean (SD) | Mean (SD) | |
| Weight, lb. | -0.8 (3.9) | -2.2 (4.9)** | 0.23 |
| BMI, kg/m² | -0.2 (1.0) | -0.2 (1.1) | 0.81 |
| Systolic blood pressure, mmHg | 5.2 (11.4)** | 5.4 (10.8)** | 0.96 |
| Diastolic blood pressure, mmHg | 4.8 (6.7)*** | 1.9 (10.2) | 0.24 |
| Pulse, beats/min | 0.2 (15.4) | -4.1 (6.8)*** | 0.21 |
| BIA scale % fat | 0.3 (3.0) | 2.1 (4.4)** | 0.10 |
| Hip circumference, in. | -0.4 (1.1) | -0.6 (3.5) | 0.82 |
| Waist circumference, in. | -0.0 (2.4) | 0.3 (2.2) | 0.64 |
| Body Fat Caliper measurement, mm | 3.8 (14.2) | 1.7 (13.4) | 0.60 |

*Independent samples t-test p-values between group comparisons
**Paired t-test p-value, p<0.05, within group comparisons
*** Paired t-test p-value, p<0.01, within group comparisons

Fig. 11

TABLE 3C: DEMOGRAPHICS, BODY MEASUREMENTS AND VITALS (Week 12)

| Variable | Active (n=22) | Placebo (n=23) | p-value* |
|---|---|---|---|
| Week 12 | Mean (SD) | Mean (SD) | |
| Weight, lb. | 186.6 (28.9)² | 190.8 (22.5) | 0.60 |
| BMI, kg/m² | 31.1 (3.2) | 30.2 (2.5) | 0.31 |
| Systolic blood pressure, mmHg | 126.8 (15.3) | 126.6 (10.5) | 0.97 |
| Diastolic blood pressure, mmHg | 79.3 (9.2) | 82.6 (9.1) | 0.25 |
| Pulse, beats/min | 74.1 (10.6) | 70.6 (8.7) | 0.24 |
| BIA scale % fat | 38.4 (9.3) | 36.1 (6.5) | 0.12 |
| Hip circumference, in. | 46.2 (4.2) | 46.0 (2.5) | 0.80 |
| Waist circumference, in. | 39.2 (4.2) | 40.0 (3.8) | 0.53 |
| Body Fat Caliper measurement, mm | 44.2 (7.0) | 38.8 (10.3) | 0.05 |
| Week 12 change from baseline | Mean (SD) | Mean (SD) | |
| Weight, lb. | -0.8 (5.7) | -1.8 (6.8) | 0.61 |
| BMI, kg/m² | -0.1 (1.0) | -0.3 (1.1) | 0.61 |
| Systolic blood pressure, mmHg | 3.2 (14.0) | 4.7 (10.4)** | 0.69 |
| Diastolic blood pressure, mmHg | 0.9 (11.0) | 5.5 (7.7)*** | 0.12 |
| Pulse, beats/min | -1.9 (16.1) | -1.3 (6.9) | 0.88 |
| BIA scale % fat | -1.3 (6.5) | 0.4 (2.3) | 0.26 |
| Hip circumference, in. | -0.6 (2.8) | 0.2 (1.4) | 0.27 |
| Waist circumference, in. | -0.2 (1.4) | 0.2 (1.6) | 0.43 |
| Body Fat Caliper measurement, mm | 4.4 (11.7) | 0.5 (12.6) | 0.30 |

*Independent samples t-test p-values between group comparisons
**Paired t-test p-value, p<0.05, within group comparisons
*** Paired t-test p-value, p<0.01, within group comparisons

Fig. 12

TABLE 4A: HUNGER AND SATIETY VAS SCORES (Baseline)

| Question | Active (n=30) Median (Interquartile range) | Placebo (n=34) Median (Interquartile range) | p-value* |
|---|---|---|---|
| Hunger Q1 (How Hungry) | | | |
| Time A | 28 (16,53) | 30 (15,44) | 0.74 |
| Time B | 49.5 (21,68) | 20 (6,46) | 0.004 |
| Hunger Q2 (Desire to eat) | | | |
| Time A | 30.5 (17,63) | 25.5 (10,38) | 0.18 |
| Time B | 44 (17,56) | 22 (5,38) | 0.004 |
| Hunger Q3 (How Full) | | | |
| Time A | 47 (26,60) | 57 (50,70) | 0.03 |
| Time B | 50 (34,61) | 61 (46,80) | 0.03 |
| Satiety Q1 (How Satisfied) | | | |
| Time A | 51 (36,65) | 50.5 (44,62) | 0.94 |
| Time B | 55 (47,80) | 54 (50,82) | 0.59 |
| Satiety Q2 (How Full) | | | |
| Time A | 53 (38,75) | 59 (49,79) | 0.33 |
| Time B | 59.5 (50,82) | 60 (42,83) | 0.82 |
| Satiety Q3 (How much can eat) | | | |
| Time A | 48.5 (36,69) | 32 (19,52) | 0.08 |
| Time B | 47.5 (18,53) | 23 (10,50) | 0.16 |
| Satiety Q4 (Desire to eat) | | | |
| Time A | 47 (19,61) | 26 (10,40) | 0.04 |
| Time B | 44.5 (18,54) | 17.5 (10,40) | 0.04 |

*Wilcoxon Rank Sum and Fisher's Exact test p-values.
** Signed rank sum t-test p-value, p<0.05
*** Signed rank sum t-test p-value, p<0.01

Fig. 13

TABLE 4B: HUNGER AND SATIETY VAS SCORES (Week 6)

| Question | Active (n=26) Median (interquartile range) | Placebo (n=24) Median (interquartile range) | p-value* |
|---|---|---|---|
| Hunger Q1 (How Hungry) | | | |
| Time A | 27.5 (15,50) | 32.5 (15,48) | 1.00 |
| Time B | 29.5 (8,51) | 34.5 (18,49.5) | 0.49 |
| Hunger Q2 (Desire to eat) | | | |
| Time A | 36 (13,46) | 30 (11,47.5) | 0.93 |
| Time B | 21 (10,49) | 38 (12.5,51.5) | 0.32 |
| Hunger Q3 (How Full) | | | |
| Time A | 62 (35,75) | 57 (41.5,68.5) | 0.39 |
| Time B | 56.5 (29,80) | 54 (29.5,69.5) | 0.60 |
| Satiety Q1 (How Satisfied) | | | |
| Time A | 61 (40,79) | 60 (46,73) | 0.66 |
| Time B | 57 (42,82) | 57 (36.5,78.5) | 0.82 |
| Satiety Q2 (How Full) | | | |
| Time A | 60 (46,82) | 61.5 (48,75) | 0.79 |
| Time B | 62.5 (47,83) | 58 (48.5,72.5) | 0.64 |
| Satiety Q3 (How much can eat) | | | |
| Time A | 38.5 (9,52)** | 44 (26,62) | 0.38 |
| Time B | 33.5 (9,57) | 43.5 (22,61.5) | 0.27 |
| Satiety Q4 (Desire to eat) | | | |
| Time A | 28 (10,51) | 34 (21,47.5) | 0.67 |
| Time B | 25.5 (11,49) | 31.5 (18.5,49) | 0.49 |
| Week 6 Change from baseline | Median (interquartile range) | Median (interquartile range) | |
| Hunger Q1 (How Hungry) | | | |
| Time A | -3.5 (-23,9) | -9 (-20,4) | 0.90 |
| Time B | -5 (-30,8)** | 3 (-8.5,9) | 0.07 |
| Hunger Q2 (Desire to eat) | | | |
| Time A | -5.5 (-27,12) | -0.5 (-13.5,10.5) | 0.32 |
| Time B | -7.5 (-36,3)** | 9 (-2.0,14) | 0.005 |
| Hunger Q3 (How Full) | | | |
| Time A | 9.5 (-13,35) | -6 (-16.5,20.5) | 0.20 |
| Time B | 7 (-12,27) | -5 (-29.5,16.5) | 0.09 |
| Satiety Q1 (How Satisfied) | | | |
| Time A | 4.5 (-12,24) | 4 (-13,24) | 0.58 |
| Time B | 1 (-7,21) | -1.5 (-17,14.5) | 0.52 |
| Satiety Q2 (How Full) | | | |
| Time A | 5.5 (-18,23) | 2 (-15,22.5) | 0.67 |
| Time B | 0.5 (-6,22) | 0 (-8.5,26) | 0.78 |
| Satiety Q3 (How much can eat) | | | |
| Time A | -5 (-39,5) | 2.5 (-14.5,22) | 0.08 |
| Time B | -2 (-29,10) | 0.5 (-10,13) | 0.39 |
| Satiety Q4 (Desire to eat) | | | |
| Time A | -5 (-46,12) | 3 (-12,21.5) | 0.13 |
| Time B | -2 (-32,5) | 1.5 (-6.5,11) | 0.12 |

*Wilcoxon Rank Sum and Fisher's Exact test.  Signed rank sum t-test p-value, p<0.05. * Signed rank sum t-test p-value, p<0.01

Fig. 14

TABLE 4C: HUNGER AND SATIETY VAS SCORES (Week 12)

| Question | Active (n=24) Median (Interquartile Range) | Placebo (n=21) Median (Interquartile Range) | p-value* |
|---|---|---|---|
| Hunger Q1 (How Hungry) | | | |
| Time A | 27 (11,39) | 27 (14,45) | 0.53 |
| Time B | 22 (10,47) | 38 (26,58) | 0.21 |
| Hunger Q2 (Desire to eat) | | | |
| Time A | 27.5 (12,45) | 28 (19,52) | 0.68 |
| Time B | 25.5 (13,46) | 34 (15,48) | 0.64 |
| Hunger Q3 (How Full) | | | |
| Time A | 56.5 (35,81) | 44 (26,60) | 0.18 |
| Time B | 59 (35,77) | 62 (40,73) | 1.00 |
| Satiety Q1 (How Satisfied) | | | |
| Time A | 70 (46,84) | 62 (45,70) | 0.62 |
| Time B | 66.5 (50,85) | 60 (49,79) | 0.58 |
| Satiety Q2 (How Full) | | | |
| Time A | 77 (49,88) | 60 (32,66) | 0.02 |
| Time B | 70 (49,85) | 61 (50,75) | 0.70 |
| Satiety Q3 (How much can eat) | | | |
| Time A | 26 (10,43) | 38 (28,52) | 0.14 |
| Time B | 35.5 (16,52) | 32 (20,50) | 0.88 |
| Satiety Q4 (Desire to eat) | | | |
| Time A | 24 (10,40) | 35 (15,52) | 0.23 |
| Time B | 31 (10,56) | 32 (10,50) | 0.53 |
| Week 12 Change from Baseline | Median (Interquartile Range) | Median (Interquartile Range) | |
| Hunger Q1 (How Hungry) | | | |
| Time A | -5 (-22,4)** | 0 (-17,11) | 0.34 |
| Time B | -9 (-36,6) | 5 (-8,27) | 0.01** |
| Hunger Q2 (Desire to eat) | | | |
| Time A | -5.5 (-30,12) | -1 (-8,11) | 0.21 |
| Time B | -11.5 (-30,5) | 4 (-11,16) | 0.03 |
| Hunger Q3 (How Full) | | | |
| Time A | 7 (-20,37) | -7 (-26,4) | 0.08 |
| Time B | 11 (-16,48) | 3 (-6,6) | 0.26 |
| Satiety Q1 (How Satisfied) | | | |
| Time A | 5 (-8,26) | 3 (-7,19) | 0.97 |
| Time B | 6 (-24,35) | 3 (-2,22) | 0.80 |
| Satiety Q2 (How Full) | | | |
| Time A | 10 (-4,33) | -6 (-19,6) | 0.02** |
| Time B | 13.5 (-23,28) | 12 (4,20)*** | 0.83 |
| Satiety Q3 (How much can eat) | | | |
| Time A | -19 (-30,-3)* | -3 (-14,7) | 0.05** |
| Time B | -7.5 (-19,6) | -7 (-13,6) | 0.68 |
| Satiety Q4 (Desire to eat) | | | |
| Time A | -9.5 (-43,1)*** | -5 (-9,14) | 0.06 |
| Time B | -5 (-16,2) | 0 (-24,7) | 0.51 |

*Wilcoxon Rank Sum and Fisher's Exact test.  Signed rank sum t-test p-value, p<0.05. *Signed rank sum t-test p-value, p<0.01.

Fig. 15

TABLE 5A: ENERGY AND MOOD VAS SCORES (Baseline)

| Question | Active (n=30) Median (interquartile range) | Placebo (n=34) Median (interquartile range) | p-value* |
|---|---|---|---|
| Energy Q1 (How tired now) Time A Time B | 36.5 (15,55) 49 (27,64) | 37.5 (20,55) 37.5 (22,65) | 0.59 0.86 |
| Energy Q2 (How tired past week) Time A Time B | 39.5 (22,64) 45 (20,67) | 49 (33,56) 50 (31,68) | 0.65 0.47 |
| Energy Q3 (How well concentrate now) Time A Time B | 71 (53,80) 68 (41,80) | 74.5 (52,80) 73 (50,80) | 0.82 0.40 |
| Energy Q4 (How well concentrate past week) Time A Time B | 64.5 (42,80) 58.5 (35,77) | 67 (50,80) 68.5 (45,80) | 0.76 0.31 |
| Energy Q5 (How well when up in morning) Time A Time B | 41 (19,70) 41.5 (19,65) | 50 (16,59) 42.5 (45,80) | 0.70 0.56 |
| Mood Q1(How nervous/anxious) Time A Time B | 17 (6,45) 14.5 (6,48) | 10.5 (18,59) 13 (4,26) | 0.21 0.32 |
| Mood Q2( How depressed/blue) Time A Time B | 9 (4,49) 10 (5,66) | 8.5 (0,25) 9 (0,26) | 0.59 0.27 |

*Wilcoxon Rank Sum and Fisher's Exact test p-values.
** Signed rank sum t-test p-value, p<0.05
*** Signed rank sum t-test p-value, p<0.01

Fig. 16

TABLE 5B: ENERGY AND MOOD VAS SCORES (Week 6)

| Question | Active (n=20) Median (Interquartile Range) | Placebo (n=24) Median (Interquartile Range) | p-value |
|---|---|---|---|
| Energy Q1 (How tired now) Time A Time B | 20.5 (10,46) 15 (10,43) | 21 (11.5,35.5) 32.5 (13.5,58) | 0.66 0.25 |
| Energy Q2 (How tired past week) Time A Time B | 21.5 (15,38) 18 (9,41) | 29.5 (17,40.5) 34 (22.50) | 0.46 0.18 |
| Energy Q3 (How well concentrate now) Time A Time B | 73 (57,83) 80 (60,84) | 75.5 (59.5,80.5) 74 (59.5,83) | 0.82 0.52 |
| Energy Q4 (How well concentrate past week) Time A Time B | 76 (64,81) 76 (50,84) | 73 (58.5,803.5) 73 (56.5,82.5) | 0.85 0.98 |
| Energy Q5 (How well when up in morning) Time A Time B | 21 (12,49) 20.5 (9,48) | 39 (20,51.5) 27 (12,47) | 0.32 0.69 |
| Mood Q1 (How nervous/anxious) Time A Time B | 15.5 (7,26) 12.5 (7,24) | 14 (6.5,38) 16.5 (5.5,22.5) | 0.82 0.88 |
| Mood Q2 (How depressed/blue) Time A Time B | 9 (5,13) 9.5 (4,16) | 10.5 (5,35) 11 (5,24) | 0.41 0.51 |
| Change from Baseline | Median (Interquartile Range) | Median (Interquartile Range) | |
| Energy Q1 (How tired now) Time A Time B | -8 (-35,7) -17 (-38,1)*** | -8 (-34.5,2)** -2 (-18,3) | 0.62 0.11 |
| Energy Q2 (How tired past week) Time A Time B | -14.5 (-34,-1)** -23 (-38,-2)*** | -13.5 (-30.5,-0.5)*** -17 (-26.5,-7)*** | 0.85 0.20 |
| Energy Q3 (How well concentrate now) Time A Time B | 8 (-2,25) 7 (-3,30)** | 3 (-4.5,12) 2 (-3.5,15.5) | 0.45 0.48 |
| Energy Q4 (How well concentrate past week) Time A Time B | 17.5 (-1,35)** 5.5 (-14,33) | 4 (-6.5,20) 5 (-9,21.5) | 0.28 0.70 |
| Energy Q5 (How well when up in morning) Time A Time B | -14.5 (-31,0) -18 (-40,2) | -6 (-38.5,11) -11 (-27.5,5) | 0.49 0.58 |
| Mood Q1 (How nervous/anxious) Time A Time B | -1 (-12,7) -2 (-19,4) | 0 (-9.5,5) -1.5 (-8,2.5) | 0.88 0.56 |
| Mood Q2 (How depressed/blue) Time A Time B | 0.5 (-15,5) -1.5 (-43,0)*** | 0 (-4.5,3.5) -2 (-8.5,1)** | 0.73 0.36 |

*Wilcoxon Rank Sum and Fisher's Exact test p-values.
** Signed rank sum t-test p-value, p<0.05
*** Signed rank sum t-test p-value, p<0.01

Fig. 17

TABLE 5C: ENERGY AND MOOD VAS SCORES (Week 12)

| Question | Active (n=2) Median (range) at Week 12 | Placebo (n=2) Median (range) at Week 12 | p-value |
|---|---|---|---|
| Energy Q1 (How tired now) | 18.5 (11,35) | 27 (7,37) | 0.83 |
| Time A | 18.5 (9,39) | 19 (9,40) | 0.77 |
| Time B | | | |
| Energy Q2 (How tired past week) | 25.5 (14,43) | 26 (16,50) | 0.78 |
| Time A | 21.5 (10,37) | 30 (13,47) | 0.38 |
| Time B | | | |
| Energy Q3 (How well concentrate now) | 68.5 (52,82) | 77 (58,83) | 0.30 |
| Time A | 57.5 (38,85) | 71 (56,88) | 0.08 |
| Time B | | | |
| Energy Q4 (How well concentrate past week) | 68.5 (52,82) | 60 (48,78) | 0.40 |
| Time A | 68 (42,84) | 70 (57,88) | 0.38 |
| Time B | | | |
| Energy Q5 (How well when up in morning) | 25 (14,51) | 33 (18,55) | 0.66 |
| Time A | 25.5 (7,44) | 25 (13,53) | 0.66 |
| Time B | | | |
| Mood Q1 (How nervous/anxious) | 21 (5,44) | 16 (9,44) | 0.85 |
| Time A | 11.5 (7,34) | 13 (8,44) | 0.79 |
| Time B | | | |
| Mood Q2 (How depressed/blue) | 10.5 (5,19) | 16 (7,45) | 0.38 |
| Time A | 13 (5,21) | 11 (7,52) | 0.73 |
| Time B | | | |
| Median Changes from Baseline | Median (range) at Week 12 | Median (range) at Week 12 | |
| Energy Q1 (How tired now) | -8 (-37,2) | -6 (-23,7)** | 0.63 |
| Time A | -17 (-54,-5)*** | -15 (-31,8) | 0.20 |
| Time B | | | |
| Energy Q2 (How tired past week) | -14.5 (-36,0)** | -5 (-33,2) | 0.52 |
| Time A | -27 (-45,-3)*** | -6 (-39,4)** | 0.29 |
| Time B | | | |
| Energy Q3 (How well concentrate now) | 5 (-21,25) | 9 (1,17)** | 0.55 |
| Time A | 0.5 (-29,27) | 9 (3,16)** | 0.25 |
| Time B | | | |
| Energy Q4 (How well concentrate past week) | 8 (-6,28) | -1 (-8,20) | 0.33 |
| Time A | 2 (-6,28) | 10 (0,19) | 0.54 |
| Time B | | | |
| Energy Q5 (How we when in morning) | -15.5 (-36,0)** | -5 (-37,8)** | 0.68 |
| Time A | -20.5 (-37,-4)** | -3 (-25,10) | 0.20 |
| Time B | | | |
| Mood Q1 (How nervous/anxious) | -0.5 (-8,19) | 0 (-8,7) | 0.88 |
| Time A | -2.5 (-22,0) | 0 (-12,13) | 0.24 |
| Time B | | | |
| Mood Q2 (How depressed/blue) | -0.5 (-19,6) | 0 (-6,5) | 0.79 |
| Time A | 0 (-30,6) | -1 (-7,2) | 0.56 |
| Time B | | | |

*Wilcoxon Rank Sum and Fisher's Exact test p-values.
** Signed rank sum t-test p-value, p<0.05
***Signed rank sum t-test p-value, p<0.01

TABLE 6A: COMPREHENSIVE METABOLIC PANEL (Baseline)

Fig. 18

| Test | Active (n=36) Mean (SD) | Placebo (n=35) Mean (SD) | p-value* |
|---|---|---|---|
| Sodium | 138.4 (21.4)² | 137.6 (2.0) | 0.18 |
| Potassium | 4.3 (0.4) | 4.4 (0.4) | 0.45 |
| Chloride | 104.5 (2.2) | 104.3 (2.2) | 0.64 |
| Carbon dioxide | 26.1 (2.9) | 25.7 (3.2) | 0.59 |
| Glucose | 88.4 (13.3) | 88.1 (12.5) | 0.90 |
| BUN | 12.8 (3.1) | 14.2 (4.8) | 0.17 |
| Creatinine | 0.84 (0.19) | 0.86 (0.21) | 0.68 |
| BUN creatinine ratio | 16.0 (5.0) | 16.7 (4.5) | 0.55 |
| Calcium | 9.6 (0.4) | 9.5 (0.4) | 0.23 |
| Total protein | 7.1 (0.4) | 7.1 (0.4) | 0.82 |
| Albumin | 4.3 (0.2) | 4.3 (0.2) | 0.79 |
| Total bilirubin | 0.52 (0.19) | 0.51 (0.21) | 0.77 |
| ALK phosphatase | 67.8 (20.0) | 61.4 (17.9) | 0.18 |
| SGOT (AST) | 21.5 (11.6) | 20.7 (14.8) | 0.81 |
| SGPT (ALT) | 21.2 (13.7) | 23.4 (23.7) | 0.64 |
| Globulin | 2.8 (0.4) | 2.8 (0.4) | 0.68 |
| A/G ratio | 1.5 (0.2) | 2.0 (2.5) | 0.29 |

*Independent samples t-test p-values

TABLE 6B: COMPREHENSIVE METABOLIC PANEL (Week 12)

Fig. 19

| Test | Active (n=36) Mean (SD) | Placebo (n=35) Mean (SD) | p-value* |
|---|---|---|---|
| Sodium | 138.7 (1.7) | 137.2 (1.9) | 0.01 |
| Potassium | 4.7 (0.6) | 4.6 (0.5) | 0.74 |
| Chloride | 104.1 (1.7) | 103.4 (1.5) | 0.20 |
| Carbon dioxide | 26.0 (3.1) | 25.4 (2.8) | 0.58 |
| Glucose | 89.9 (14.7) | 89.5 (13.8) | 0.93 |
| BUN | 12.8 (2.8) | 12.8 (3.8) | 1.00 |
| Creatinine | 0.85 (0.14) | 0.88 (0.22) | 0.61 |
| BUN creatinine ratio | 15.2 (3.5) | 14.7 (3.3) | 0.63 |
| Calcium | 9.8 (0.4) | 9.6 (0.4) | 0.18 |
| Total protein | 7.3 (0.4) | 7.3 (0.4) | 0.74 |
| Albumin | 4.4 (0.2) | 4.3 (0.2) | 0.24 |
| Total bilirubin | 0.53 (0.22) | 0.54 (0.13) | 0.91 |
| ALK phosphatase | 71.3 (23.2) | 64.9 (18.2) | 0.36 |
| SGOT (AST) | 22.2 (11.3) | 21.8 (10.5) | 0.92 |
| SGPT (ALT) | 23.0 (14.7) | 25.7 (16.3) | 0.59 |
| Globulin | 2.9 (0.4) | 3.0 (0.4) | 0.31 |
| A/G ratio | 1.6 (0.2) | 1.5 (0.2) | 0.22 |

*Independent samples t-test p-values

Fig. 20

TABLE 8: NUMBER OF TIMES EXERCISED

| Time Interval | Active (n=25) Mean (SD) | Placebo (n=25) Mean (SD) | p-value* |
|---|---|---|---|
| Week 6 | 4.4 (1.5) | 4.3 (1.1) | 0.74 |
| Week 12 | 4.6 (1.3) | 4.3 (1.5) | 0.43 |
| Total over weeks 1 – 12 | 53.5 (13.6) | 48.6 (17.5) | 0.29 |

*Independent samples t-test p-values

Fig. 21

TABLE 9: SUBJECT REPORTED SIDE EFFECTS

| Week 6 | Active (n=25) | Placebo (n=25) | p-value* |
|---|---|---|---|
| 1. Nausea | 3 | 1 | 0.61 |
| 2. Flushing | 1 | 0 | 1.00 |
| 3. Feeling hot | 3 | 3 | 1.00 |
| 4. Somnolence (sleepiness) | 4 | 3 | 1.00 |
| 5. Headache, any | 3 | 4 | 1.00 |
| 6. Headache, more than normal | 1 | 3 | 0.61 |
| 7. Excessive sweating | 4 | 3 | 1.00 |
| 8. Insomnia, difficulty falling asleep | 4 | 3 | 1.00 |
| 9. Insomnia, difficulty staying asleep | 3 | 5 | 0.70 |
| 10. Any other side effects | 1 | 1 | 1.00 |
| Total subjects with side effects – week 6 | 11 (44.0%) | 14 (56%) | 0.40 |

| Week 12 | Active (n=25) | Placebo (n=21) | p-value* |
|---|---|---|---|
| 1. Nausea | 1 | 1 | 1.00 |
| 2. Flushing | 1 | 0 | 1.00 |
| 3. Feeling hot | 4 | 1 | 0.35 |
| 4. Somnolence (sleepiness) | 1 | 6 | 0.04 |
| 5. Headache, any | 3 | 4 | 0.69 |
| 6. Headache, more than normal | 3 | 1 | 0.61 |
| 7. Excessive sweating | 3 | 2 | 1.00 |
| 8. Insomnia, difficulty falling asleep | 2 | 3 | 0.65 |
| 9. Insomnia, difficulty staying asleep | 2 | 4 | 0.40 |
| 10. Any other side effects | 1 | 0 | 1.00 |
| Total subjects with side effects – week 12 | 7 (29.2%) | 9 (42.9%) | 0.34 |

*Chi-square and Fisher's Exact test p-values

WHOLE GREEN COFFEE BEAN PRODUCTS AND METHODS OF PRODUCTION AND USE FOR PREVENTING OR TREATING OBESITY AND DIABETES

CROSS-REFERENCE TO RELATED APPLICATIONS

This application is a Continuation-in-Part of U.S. patent application Ser. No. 14/716,869 Filed on May 19, 2015, which issued as U.S. patent Ser. No. 10/086,031 on Oct. 2, 2018, which is a Continuation-in-Part of U.S. patent application Ser. No. 13/215,174 filed on Aug. 22, 2011, which issued as U.S. Pat. No. 9,034,410 on May 19, 2015.

STATEMENT REGARDING FEDERALLY SPONSORED RESEARCH OR DEVELOPMENT

Not Applicable.

NAMES OF PARTIES TO A JOINT RESEARCH AGREEMENT

Not Applicable

REFERENCE TO SEQUENCE LISTING, A TABLE, OR A COMPUTER PROGRAM LISTING APPENDIX SUBMITTED ON A COMPACT DISC AND INCORPORATION-BY-REFERENCE OF THE MATERIAL

Not Applicable.

COPYRIGHT NOTICE

Not Applicable

BACKGROUND OF THE INVENTION

Field of the Invention

The present invention relates to methods of processing green coffee beans, products obtained and defined by those methods, and methods of treatment using those products.

Description of the Related Art

Worldwide, caffeine is the most widely consumed substance having psychoactive effects. It is the neuroactive agent in coffee and tea, and it is a nonselective antagonist of the neuromodulator adenosine; if applied in commonly consumed doses, it generates stimulating effects by blockading adenosine receptors. Cognitive performance generally is positively influenced by caffeine ingestion, and the influence of caffeine on cognitive performance is well documented. Although some studies show limited benefit to performance, caffeinated coffee is the most common form of caffeine intake, increasing alertness and lowering fatigue. Caffeine is now readily available in a variety of liquid (ie, energy drinks) and capsule forms.

The term "coffee bean" collectively refers to the seeds (coffee seeds) that are obtained by the refining process of removing the pulp and the skin from the berries (known as coffee berries or coffee cherries) of *Coffea* plants, and the beans that are produced from these. Coffee berries, which contain the coffee bean, are produced by several species of small evergreen plants of the genus *Coffea*, which are of the family Rubiaceae. The two most commonly grown species are *Coffea robusta* (also known as *Coffea canephora*) and *Coffea arabica*. These are typically cultivated in Latin America, Southeast Asia, and Africa. "Green" coffee beans are coffee beans that have not yet passed through a roasting process, such as the roasting process used in the production of coffee.

The various steps in the production of coffee are described in Smith, A. W., in Coffee; Volume 1: Chemistry pp 1-41, Clark, R. J. and Macrea, R. eds, Elsevier Applied Science London and New York, 1985; Clarke, R. J., in Coffee: Botany, Biochemistry, and Production of Beans and Beverage, pp 230-250 and pp 375-393; and Clifford, M. N. and Willson, K. C. eds, Croom Helm Ltd, London, as described in U.S. patent application Ser. No. 12/941,557 titled Modulation Of Coffee Flavour Precursor Levels In Green Coffee Grains, filed Nov. 8, 2010 on behalf of McCarthy, et al., and published on May 26, 2011 as publication number U.S. 2011/0126314 A1 (hereafter "McCarthy"), the entirety of which is incorporated herein by reference as though set forth in full herein. The process typically starts with the collection of mature, ripe red coffee cherries. The outer layer, or pericarp, can then be removed using either the dry or wet process. The dry process is the simplest and involves: (1) classification and washing of the cherries; (2) drying the cherries after grading (either air drying or mechanical drying); and (3) dehusking the dried cherries to remove the dried pericarp. The wet process is slightly more complicated, and generally leads to the production of higher quality green beans. The wet process is more often associated with *C. arabica* cherries. The wet process may comprise: (A) classification of the cherries; (B) pulping of the cherries (this step is done soon after harvest and generally involves mechanical removal of the "pulp", or pericarp, of the mature cherries); (C) "fermentation," where the mucilage that remains attached to the grain of the cherries after pulping is removed by allowing the grain plus attached mucilage to be incubated with water in tanks using a batch process. The "fermentation" process is allowed to continue up to 80 hours, although often 24 hours is generally enough to allow an acceptable fermentation and to cause the pH to drop from around 6.8-6.9 to 4.2-4.6, due to various enzymatic activities and the metabolic action of microorganisms which grow during the fermentation. The next steps, (D) drying, involves either air or mechanical hot air drying of the fermented coffee grain, and (E) "hulling," involves the mechanical removal of the "parch" of the dried coffee grain (dried parchment coffee) and often the silverskin. After wet or dry processing, the resulting green coffee grain are often sorted, with most sorting procedures being based on grain size and/or shape.

The next step in the production of conventional coffee is the roasting of the green grain after dehusking or dehulling of dry or wet processed coffee, respectively. This is a time-dependent process which induces significant chemical changes in the bean. The first phase of roasting occurs when the supplied heat drives out the remaining water in the grain. When the bulk of the water is gone, roasting proper starts as the temperature rises towards 374-392 degrees Fahrenheit. The degree of roasting, which is usually monitored by the color development of the beans, plays a major role in determining the flavor characteristics of the final beverage product. Thus, the time and temperature of the roasting are tightly controlled in order to achieve the desired coffee flavor profile. After roasting, the coffee is ground to facilitate extraction during the production of the coffee beverage or coffee extracts (the latter to be used to produce instant coffee products). Again, the type of grinding can influence the final characteristics of the product, such as the flavor of the beverage.

While a considerable amount of research has been carried out on the identification of the flavor molecules in coffee, much less work has been done regarding the physical and chemical reactions that occur within the coffee grains during each of the processing steps. This latter point is particularly evident for the roasting reaction, where the large number of grain constituents undergo an extremely complex series of heat induced reactions (Homma, S. 2001, In "Coffee: Recent Developments". R. J. Clarke and O. G. Vitzthum eds, Blackwell Science, London; Yeretzian, C., et al ((2002) Eur. Food Res. Technol. 214, 92-104; Flament, I (2002) Coffee Flavor Chemistry, John Wiley and Sons, UK; Reineccius, G. A., "The Maillard Reaction and Coffee Flavor" Conference Proceedings of ASIC, 16th Colloque, Kyoto, Japan 1995).

While the details of most of the reactions that occur during the different steps of coffee processing remain relatively unclear, it is understood that the conventional roasting process likely destroys or degrades many beneficial components present in green coffee beans, including phytonutrients such as, for example, Chlorogenic acid. Chlorogenic acids (CGA) are a family of esters formed between certain hydroxycinnamic acids (i.e. caffeic and feluric acids) and (−)-quinic acid. Green (or raw) coffee is a major source of CGA in nature (5-12 g/100 g) (Farah et al. Braz J Plant Physiol. 365 2006; 18:23-36). The major CGA in green coffee are 3-, 4- and 5-caffeoylquinic acids (3-, 4- and 5-CQA), 3,4-, 3,5- and 4,5-dicaffeoylquinic acids (3,4-, 3,5-, and 4,5-diCQA); 3-, 4- and 5-feruloylquinic acids (3-, 4- and 5-FQA) and 3-, 4- and 5-p-coumaroylqunic acids (3-, 4-, and 5-p-CoQA). Caffeoylferuloylquinic acids (CFQA) are minor CGA compounds also found in green coffee, especially in *Coffea robusta* species, as described in U.S. patent application Ser. No. 263292 titled Effects Of A Decaffeinated Green Coffee Extract On Body Weight Control By Regulation Of Glucose Metabolism, filed Oct. 31, 2008 on behalf of Lemaire, et al., and published on May 6, 2010 as publication number U.S. 2010/0112098 A1 (hereafter "Lemaire"), the entirety of which is incorporated herein by reference as though set forth in full herein. Very small amounts of CGA lactones formed by heating during primary processing may also be observed (Farah et al. Braz J Plant Physiol. 2006, 18:23-36.—Farah et al. J Agric Food Chem. 2005; 53:1505-13).

While green coffee beans have recently been recognized to have some potentially important health benefits (see, e.g., Lemaire, above), products created from green coffee beans have not been widely available like roasted coffee. Part of the reason for this is that processing, preserving and packaging coffee beans in their nutritious, unroasted, "green" state has been difficult, expensive and generally not feasible. For example, Lemaire teaches only extracting certain substances from the green coffee bean, not processing of the entire green coffee bean.

Accordingly, what is needed is an improved method of processing green coffee beans, including partial or whole green coffee beans, that can be used to more easily and inexpensively create green coffee bean products, such as capsules, tablets, mixes, additives, supplements, and the like. Such an improved method is needed to unlock the potential health benefits to consumers of relatively inexpensive products created with green coffee beans, especially whole green coffee beans.

Attention Disorders: Individuals progressing through academic study require concerted focused attention in order to successfully master the tasks posed by school. Control of attention is managed by executive functions that help to prioritize, organize, and complete work in a timely way. Russell Barkley describes executive functions as the actions people use to control personal behavior, direct behavior toward a goal, and improve outcomes for behavior in the future. The role of attention in executive functions is critical in most facets of organized daily life.

Attention wandering compromises executive functions and results in cognitive difficulties in learning. Attention problems are certainly evident, for example, in attention-deficit/hyperactivity disorder (ADHD) which is a developmental disorder in children, and, to varying degrees in adults. The etiology and impact of poor attention is multifactorial and impacts school performance of children, adolescents, and young adults. Alternative and complementary treatments may be helpful in managing behaviors associated with attention to school tasks, thus it is useful to investigate them.

Diabetes: Diabetes is the most frequent metabolic disorder in the world population occurring in 422 million people in 2014. Non-insulin-dependent diabetes mellitus (NIDDM) accounts for approximately 90 percent of all cases. In 2015, 1.6 million deaths were directly attributable to diabetes, and an additional 2.2 million deaths were linked to high serum glucose levels. Diabetes mellitus is a chronic disorder of metabolism which occurs when the pancreas cannot produce enough insulin to regulate blood sugar. Insulin resistance is a key feature of NIDDM. In the early stages of the illness the body can compensate by increasing insulin secretion from the pancreas. Over time the body's ability to compensate fails, and serum glucose levels begin to rise. Once fasting serum glucose levels reach 7.0 mmol/1 Type 2 Diabetes Mellitus is diagnosed in accordance with ADA guidelines. Over time high glucose levels damage nerves and blood vessels. Atherosclerosis is commonly associated with NIDDM, and eventually leads to cardiovascular disease.

Obesity: The Center for Disease Control (CDC), defines obesity as an excess amount of adipose tissue in relation to lean body mass (1). According to the National Health and Nutrition Examination Survey (NHANES), 61% of the U.S. population is either overweight or obese (1). NHANES II and NHANES 1999 data indicate that the prevalence of overweight people in the U.S. (20-74 years) was 35% in 1999 and that for obese 27%, almost twice the 15% number in 1980. Those who are obese are more likely to experience kidney trouble, diabetes, high blood pressure, heart disease, pregnancy complications, psychological problems, sudden death, obstructive sleep apnea, Pickwickian Syndrome, congestive heart failure, limited daily activities, and liver damage (2-4).

These facts taken together indicate that obesity represents not only a risk to the individual obese patient but also a challenge to an already strained health care system. As a result many novel pharmacological and surgical means are being deployed in the war against fat, including dietary supplement preparations.

Accordingly, what is needed are improved methods of preventing and treating diabetes and obesity.

BRIEF SUMMARY OF THE INVENTION

Disclosed are novel processing methods for green coffee beans that result in novel green coffee bean products, including products that incorporate whole green coffee beans. Green coffee bean products created and defined by these methods have unexpectedly been found to increase focus and concentration in users, and are believed useful in the treatment of attention deficits. Accordingly, provided herein are novel methods of treatment using green coffee beans and related products comprising whole green coffee beans to increase focus and concentration in users, and to treat attention and concentration deficits and related disorders, such as attention deficit (AD), attention deficit disorder (ADD), attention deficit hyperactivity disorder (ADHD), and various related and/or comorbid disorders.

More specifically, provided in certain embodiments is a method of processing whole green coffee beans to create stabilized whole green coffee bean mixtures, that includes the steps of: selecting whole coffee beans in their fresh green unroasted state with naturally-occurring levels of phytonutrients; sterilizing the coffee beans; reducing the moisture content of the coffee beans; grinding the coffee beans; and mixing at least one stabilizer into the ground coffee beans; wherein all of the aforesaid steps are accomplished without exposing the coffee beans to high enough temperatures for a sufficient amount of time to substantially degrade the naturally-occurring levels of phytonutrients in the coffee beans. In certain embodiments, all of the aforesaid steps are accomplished without exposing the coffee beans to temperatures exceeding about 130 degrees Fahrenheit for more than a few seconds. The whole green coffee beans may comprise *Coffea robusta* coffee beans, and the phytonutrients may include Chlorogenic acid, including in some embodiments at least two percent by weight of Chlorogenic acid. The step of reducing the moisture content of the coffee beans may comprise reducing the moisture content of the coffee beans to less than about two percent. The at least one stabilizer may comprises at least one of, or all of, Magnesium Silicate; Silicon Dioxide; Tricalcium Phosphate.

In various embodiments, the step of grinding the coffee beans may comprise a plurality of iteratively finer grinding steps, such as three increasingly fine steps. For example, the step of grinding the coffee beans may result in most of the ground coffee bean material being sized to pass through a 20 mesh screen.

Also provided are stabilized whole green coffee bean mixtures that necessarily results from and is defined by the foregoing processes. The stabilized whole green coffee bean mixtures may be packaged into at least one of the following forms: packaged in bulk powder form; compressed into a tablet; inserted into a capsule; or mixed with another nutritional supplement or product.

A method is also provided that increases the concentration of and focuses the attention of a user, that includes the step of administering an amount of stabilized whole green coffee bean mixture effective to treat the user.

In another embodiment, a stabilized whole green coffee bean powder is used to treat or prevent diabetes.

In another embodiment, a stabilized whole green coffee bean powder is used to treat or prevent obesity.

These and other objects and advantages of the present invention will become apparent from a reading of the attached specification and appended claims. There has thus been outlined, rather broadly, the more important features of the invention in order that the detailed description thereof that follows may be better understood, and in order that the present contribution to the art may be better appreciated. There are features of the invention that will be described hereinafter and which will form the subject matter of the claims appended hereto.

BRIEF DESCRIPTION OF THE DRAWINGS

Further features, advantages and characteristics of the present invention will become apparent to a person of ordinary skill in the art in view of the following detailed discussion of example embodiments of the present invention, made with reference to the drawings annexed, in which:

FIG. 7 shows a chart of the schedule of events used in testing the effect of WGCP on obesity in accordance with the principles of the invention;

FIG. 8 shows a flow chart of a protocol used in testing the effect of WGCP on obesity in accordance with the principles of the invention;

FIG. 9 shows a chart of the demographics of the test subjects used in testing the effect of WGCP on obesity in accordance with the principles of the invention;

FIG. 10 shows a chart of the demographics, body measurements and vital signs of the test subjects used in testing the effect of WGCP on obesity at week 6 in accordance with the principles of the invention;

FIG. 11 shows a chart of the demographics, body measurements and vital signs of the test subjects used in testing the effect of WGCP on obesity at week 12 in accordance with the principles of the invention;

FIG. 12 shows a chart of feedback from the test subjects at the beginning of a study used in testing the effect of WGCP on obesity in accordance with the principles of the invention;

FIG. 13 shows a chart of feedback from the test subjects at week 6 of a study used in testing the effect of WGCP on obesity in accordance with the principles of the invention;

FIG. 14 shows a chart of feedback from the test subjects at week 12 of a study used in testing the effect of WGCP on obesity in accordance with the principles of the invention;

FIG. 15 shows a chart of feedback from the test subjects at the beginning of a study used in testing the effect of WGCP on obesity in accordance with the principles of the invention;

FIG. 16 shows a chart of feedback from the test subjects at week 6 of a study used in testing the effect of WGCP on obesity in accordance with the principles of the invention;

FIG. 17 shows a chart of feedback from the test subjects at week 12 of a study used in testing the effect of WGCP on obesity in accordance with the principles of the invention;

FIG. 18 shows a chart of metabolism in the test subjects at the beginning of a study used in testing the effect of WGCP on obesity in accordance with the principles of the invention;

FIG. 19 shows a chart of metabolism in the test subjects at week 12 of a study used in testing the effect of WGCP on obesity in accordance with the principles of the invention;

FIG. 20 shows a chart of exercise performed by test subjects of a study used in testing the effect of WGCP on obesity in accordance with the principles of the invention;

FIG. 21 shows a chart and reported side effects during a study used in testing the effect of WGCP on obesity in accordance with principles of the invention.

DETAILED DESCRIPTION

Figure 1:
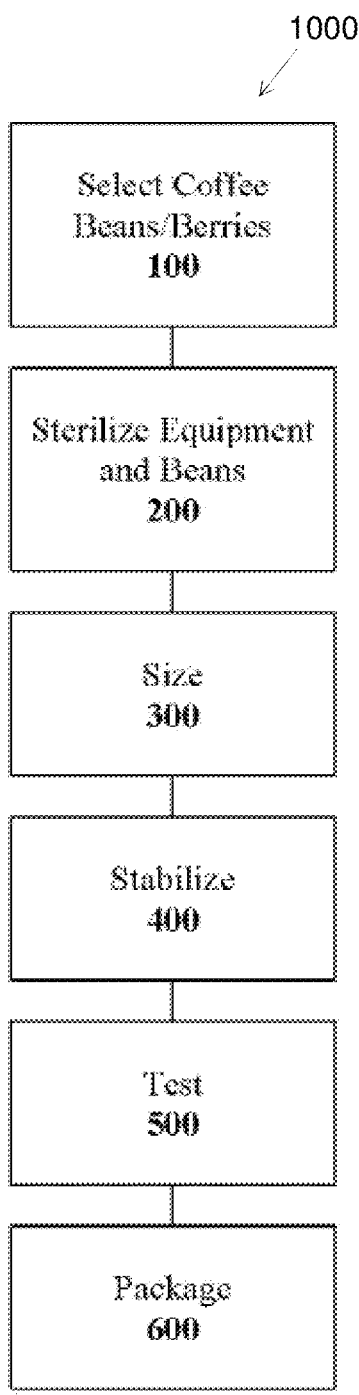
FIG. 1 provides a flow chart showing example steps of a method for processing whole green coffee beans and generating resulting whole green coffee bean products.

Before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

FIG. 1 shows a process 1000 for preparing whole or partial green coffee beans for tableting, encapsulation, and or other nutritional uses such as mixes, additives, supplements, and the like. Process 1000 has been developed to tend to preserve the Chlorogenic Acid and other phytonutrient content of the green coffee beans by using relatively low temperatures, for instance in one example not more than about 130 degrees Fahrenheit, throughout the processing steps.

Step 1—Berry Selection:

The first step in process 1000 is berry selection 100. Whole coffee beans are selected in their fresh green unroasted state, preferably with high levels of Chlorogenic Acid and other naturally occurring phytonutrients. For example, the *Coffea robusta* species of berries may be selected. However, any suitable berry or combination of berries may be selected.

Figure 2:
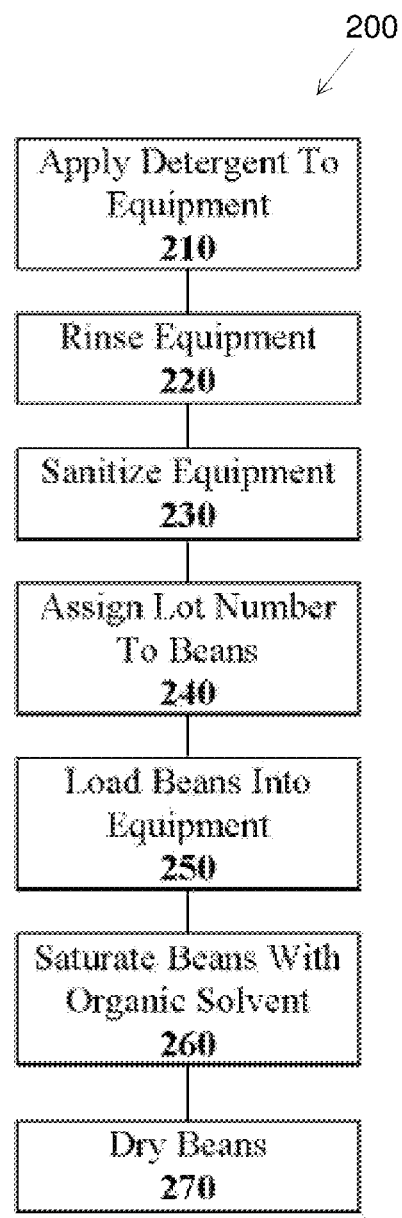
FIG. 2 provides a flow chart showing example sterilization steps of a method for processing whole green coffee beans and generating resulting whole green coffee bean products.

Step 2—Sterilization:

Turning to FIG. 2, in the second step, sterilization 200, the processing machinery must be sterilized. The machinery, such as a ribbon mixer, should be sanitized to make certain that it is clean and free from any debris from products that were processed prior to green coffee. The machinery may also be cleaned with an industrial strength sanitizing solution that kills microbial contamination. In one embodiment, the machinery comprises a Weiler & Company Model 1660 thirty cubic foot ribbon mixer that may be cleaned in a three-step process. In step one, the detergent phase 210, the mixer may be cleaned with trisodium phosphate or similar substance to remove any filth or debris. In step two, clear water rinse 220, the mixer is rinsed thoroughly with clean potable water to remove any detergent residue. Then in step three, the sanitizing phase 230, all food contact surfaces may be saturated with alcohol or other appropriate organic solvent, such as a 70% isopropyl alcohol (IPA) solution, and allowed to air dry.

The whole green coffee beans may have a lot number assigned 240 for the purposes of batch control, for instance in compliance with current Good Manufacturing Practices for Dietary Supplements (cGMP), pursuant to 21 CFR 111. A predetermined amount of the green coffee beans are loaded 250 in the equipment, such as a properly sanitized ribbon mixer. For example, in one embodiment, 100 to 300 kilograms of whole green coffee beans are loaded 250 into a properly sanitized thirty cubic foot ribbon mixer.

The whole green coffee beans are then saturated 260 with an appropriate organic solvent such as IPA. The saturated beans are then dried 270 in a hygienic manner. The saturated beans may be dried by, for instance, removing them from the ribbon mixer and placing them evenly on clean paper-lined trays that are placed in drying racks. The drying Racks may then be moved into a climate controlled drying room set at, for instance, 120-130 degrees Fahrenheit, until they are completely dried. This may take approximately twelve to twenty-four hours, for example to reduce the moisture level of the beans from a typical fifteen percent to less than, for example, two percent.

While example sterilization steps have been provided above, any suitable means of sterilization may be used. A means of sterilization should be suitable if it sufficiently kills yeast, mold, bacteria, and viral contamination that may be present on the beans. This is preferably done for the safety of those consuming the product, and for the purpose of extending the shelf life of the products of which the green coffee beans will become a part. The heating and/or drying aspect 270 of the example process also serves to extend shelf life, as well as to expedite the steps that follow.

Figure 3:
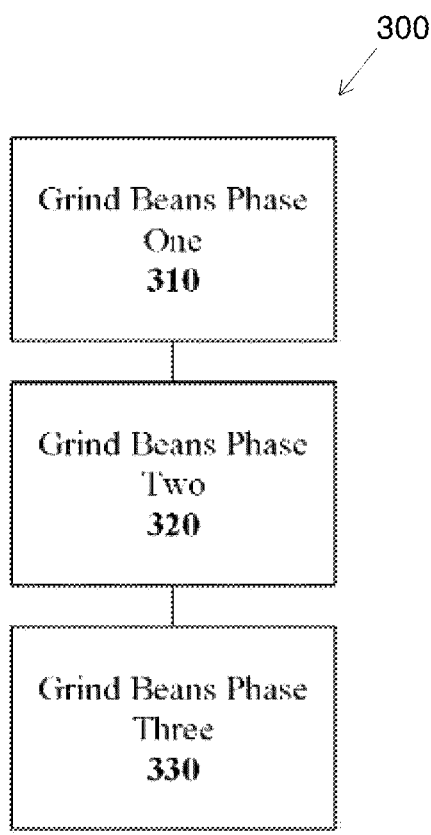
FIG. 3 provides a flow chart showing example sizing steps of a method for processing whole green coffee beans and generating resulting whole green coffee bean products.

Step 3—Sizing:

The third step, sizing 300, an iterative example of which is illustrated in FIG. 3, may be performed using a coffee-grinding mill. Typical coffee-grinding mills tend to generate a great deal of friction and heat. In order to keep the temperature of the beans relatively low during this process, for instance under about 130 degrees Fahrenheit, the whole green coffee beans may be ground down to successively smaller sizes in a plurality of iterative phases. For example, one embodiment employs three iterative phases. In Phase One 310, the sterilized and dried beans are passed through a grinder, such as a Modern Process Equipment 3 HP Coffee Grinder, reducing the size of the bean to, for instance, a minus 8-10 mesh screen size. Then in Phase Two 320, the grinder setting is reduced, for instance from course setting 1 to 3, and the Phase One material is passed through the grinder, further reducing the size so that the material will pass through, for instance, a 12-16 mesh screen. Next, in Phase Three 330, the grinder setting is reduced again, for instance from a course setting 3 to a medium setting in the range of 3 to 7, and the Phase Two material is passed through the mill again until all of the material passes through a smaller screen, such as, for instance, a 20 mesh screen.

Like the other examples provided herein, the above example sizing step 300 is just illustrative of the concept, and the invention is not limited to any of these specific steps unless otherwise stated in the claims. The point is that grinding or milling green coffee is difficult. To preserve its nutritional integrity during the sizing step 300, the green coffee material should not be forced through the mill in a manner that would generate excessive heat, for instance heat that would raise the temperature of the green coffee material above about 130 degrees Fahrenheit. For example, instead of filling or stuffing the grinder with green coffee material and letting it grind, green coffee material can be introduced to the grinder at approximately the same rate as the grinder grinds it on a particular setting.

Note that higher temperatures could be used at various steps and still fall within the scope of the invention, however incremental degradation of the green coffee would likely start to occur according to a time-temperature relationship. For example, the green coffee beans/material may be able to be subject to temperatures exceeding 130 degrees Fahrenheit for several seconds without materially degrading its nutritional components.

Figure 4:
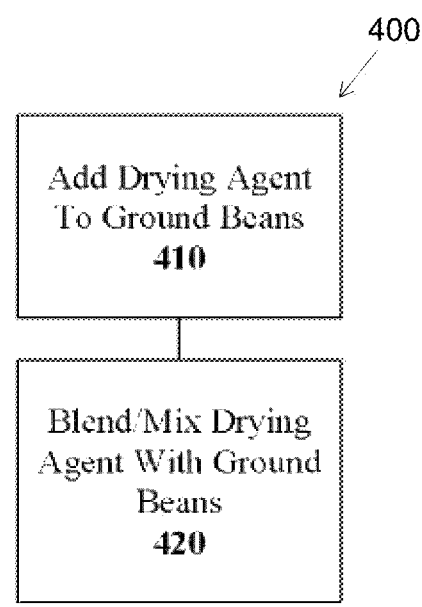
FIG. 4 provides a flow chart showing example steps of a method for stabilizing whole green coffee beans and generating resulting whole green coffee bean products.

Step 4—Stabilization:

Next, the finely ground whole green coffee bean material may be stabilized 400 as illustrated in FIG. 4. During this step 400 the whole green coffee beans that have been ground and classified to predetermined specifications as described above may be placed in a properly sanitized blender. For example, the green coffee bean material may be placed in a Patterson Kelley Twin V sixty-five cubic foot blender that has been sanitized using the three-step process 210, 220, 230 described above. A drying agent may then be introduced 410 to the green coffee bean material. Suitable drying agents may include, for example, Magnesium Silicate, Silicon Dioxide, Tricalcium Phosphate, and the like.

In one example embodiment of the stabilization step 400, six hundred kilograms of sterilized and ground green coffee is placed into a sterilized Patterson Kelley Twin V sixty-five cubic foot blender. Added into the ground green coffee in this example is one to two percent each (by weight) of Magnesium Silicate, Silicon Dioxide, and Tricalcium Phosphate through a 12 mesh screen. That combination may then blended or mixed 420 for ten minutes at twenty-four revolution per minute, creating an example stabilized whole green coffee bean mixture.

While example stabilization steps 410, 420 are described above, any suitable stabilization procedure may be used. Suitable stabilization procedures are those that assist in the long-term preservation of the whole green coffee bean material, as well as the Chlorogenic acid, essential oils and other phytonutrients naturally present in the green coffee beans. Suitable stabilization procedures also typically provide an anti-caking effect that tends to keep the material from clumping when in storage, and tends to provide a free-flowing powder that facilitates the material being tableted, encapsulated, or otherwise used in nutritional products.

Figure 5:
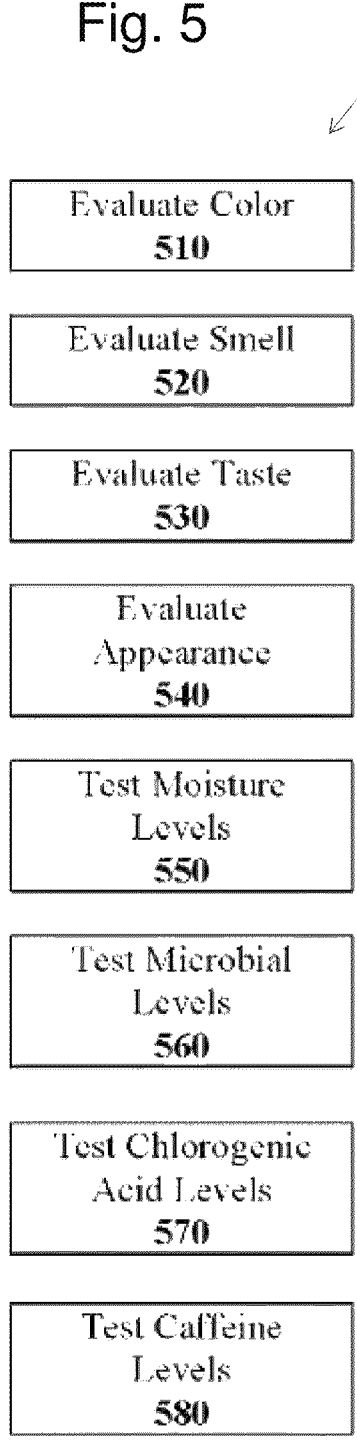
FIG. 5 provides a flow chart showing example steps of a method for testing whole green coffee beans and generating resulting whole green coffee bean products.

Step 5—Testing:

Portions of the stabilized whole green coffee bean mixtures may be tested 500, as shown in FIG. 5. Several parameters may be tested or otherwise evaluated in any appropriate order, including, for example, color 510, odor 520, taste 530, appearance 540, moisture levels 550, microbial levels 560, Chlorogenic acid levels 570, caffeine levels 580, and any other suitable testing, for instance as may be required for various nutritional applications.

For example, color testing 510 may be accomplished by matching the color of the material to a light green laboratory control sample. The material passes if it is the typical color of ground green coffee. The material fails if it is not the typical color of ground green coffee. Similarly, odor or smell testing 520 may be accomplished by, for example, matching the smell of the material to a laboratory control sample. The material passes if it has the typical odor of ground green coffee. The material fails if it does not have the typical odor of ground green coffee. Likewise, taste testing 530 may be accomplished by, for example, matching the taste of the material to a laboratory control sample. The material passes if it has the typical taste of ground green coffee. The material fails if it does not have the typical taste of ground green coffee.

Appearance testing 540 may be accomplished by, for example, passing the material through a 20 mesh screen. The material may be considered to pass if 99% or more passes through the screen.

Moisture level testing 550 may be accomplished by, for example, testing the moisture level of the material. The material may be considered to pass if the moisture level is not more than two percent.

Microbial level testing 560 may be accomplished in various way, including, for example, passing the material if it has a total plate count of not more than 1000, yeast and mold test negative, and coliform tests negative.

Chlorogenic acid level testing 570 may be accomplished using known means.

The material may be considered to pass if, for instance, the Chlorogenic acid levels are not less than two percent.

Caffeine level testing 580 may be accomplished using known means. What levels are considered to pass may change in view of the caffeine level desired in the finished product. Unless otherwise specified, the caffeine level should be the same as naturally occurs in green coffee beans.

The above testing regimens are examples only and are not limiting. Any suitable testing may be performed at any stage of the process 1000.

Figure 6:
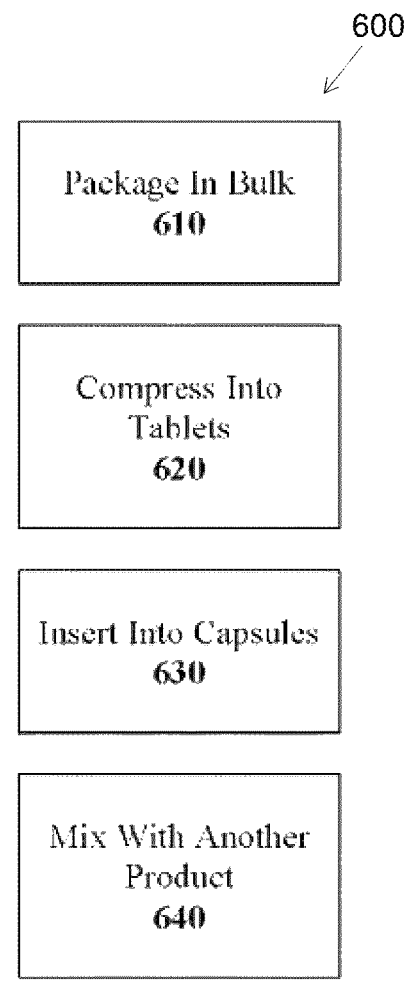
FIG. 6 provides a flow chart showing example steps of a method for packaging whole green coffee beans and generating resulting whole green coffee bean products.

Step 6—Packaging:

The stabilized whole green coffee bean mixtures described above may be packaged 600 in any of numerous ways, some of which are shown in FIG. 6, and many of which are made possible, or at least especially easier, by the foregoing steps. The stabilized whole green coffee bean mixtures may be packaged as oral dosage forms in typical dietary supplement format, added to foods, and/or delivered in a medium for topical, cosmetic use (such as in a cream or ointment, for example). If the stabilized whole green coffee bean mixture is to be consumed directly (as a food additive, for example), it may be flavored, and thereby serve as a dual-purpose product (as a drink-flavoring agent, for example).

For example and not by way of limitation, in certain embodiments the unique and novel stabilized whole green coffee bean mixtures may be packaged 610 in bulk powder form, may be readily compressed 620 into tablets, may be readily inserted 630 into capsules, or may be mixed 640 with another nutritional supplement or product.

Use Treating Attention Deficit Disorders:

A method of treatment using whole green coffee beans and products comprising whole green coffee beans has unexpectedly been found to dramatically increase focus and concentration in users, and is believed useful in the treatment of attention deficits. Accordingly, provided herein are novel methods of treatment using green coffee beans and related products comprising whole green coffee beans to increase focus and concentration in users, and to treat attention and concentration deficits and related disorders, such as attention deficit (AD), attention deficit disorder (ADD), attention deficit hyperactivity disorder (ADHD), and various related and/or comorbid disorders.

For example and not by way of limitation, the unique and novel stabilized whole green coffee bean mixtures described herein may be administered to a user, for instance orally, to increase the person's focus and concentration. In fact, it has been discovered that certain users may replace their prescription medications for ADD/ADHD with green coffee beans and related products comprising whole green coffee beans. Factors that may be considered in determining suitability and appropriate dosage include the user's age, weight, and other medications the user may be taking, as would be apparent to a person of skill in the art when provided with the present disclosure. For example, it initially appears that users may be able to replace prescription medications for ADD/ADHD with green coffee beans and related products comprising whole green coffee beans, such as, for example, the unique and novel stabilized whole green coffee bean mixtures described herein, unless, for instance, the user is also taking anti-depressants.

In one specific example embodiment, a treatment protocol may comprise a user orally consuming the unique and novel stabilized whole green coffee bean mixtures described herein in the form of tablets, capsules, or any other suitable delivery means, where the dosage contains about fifty-five milligrams of caffeine per dosage. In that example protocol, a user may take one dosage in the morning and one in the afternoon for two consecutive days. If the user has then not yet experienced satisfactory results, the user may continue the treatment with two dosages in the morning and two in the afternoon for two consecutive days. If the user still has then not yet experienced satisfactory results, the user may continue the treatment with three dosages in the morning and three in the afternoon for two consecutive days. It has been found that the above example treatment protocol provides satisfactory results for the vast majority of users. In the rare instances where this protocol is not satisfactory, three dosages may be taken three times a day. It is believed that most users may take three of the above example dosages four times a day without adverse effect.

Using the example dosages provided in the specific embodiment provided above, other example treatment protocols may include: one or two dosages twice a day for persons twelve to sixteen years of age; two dosages in the morning and one dosage in the early afternoon for persons sixteen to eighteen years of age; and two or three dosages in the morning and two dosages in the early afternoon for persons eighteen years of age and older.

All the foregoing dosages and treatment regimens are examples only, and do not limit the scope of the invention except where specifically claimed. Any user, especially those allergic or sensitive to caffeine, should consult with their physician before consuming any of the materials described herein, as with any dietary or energy supplement, and children under the age of eighteen should only consume such products under adult supervision. Products such as those disclosed herein should likely be avoided by those who are or may be pregnant or lactating. Dosages may be self-administered by a user or administered by someone else to a user.

Consuming whole green coffee beans and related products that comprise whole green coffee beans provides unexpected synergistic results compared to traditional coffee products. For example, in the specific examples provided above, three dosages comprise about 165 milligrams of caffeine, which is approximately equivalent to a traditional cup of coffee. But while the primary stimulative effects of a cup of coffee only last about twenty to thirty minutes, consuming three of the example doses described above provides greatly increased concentration and attention that lasts about four to five hours.

Consuming whole green coffee beans as a solid is believed to provide a natural time-release effect as shown in Figures, taking about fifteen minutes to begin and lasting for several hours, compared to consuming traditional coffee as a liquid, which causes a rapid up-and-down effect. Consuming products comprising whole green coffee beans, i.e, manufactured from the entire bean, also provides far superior results to consuming chemicals extracted or isolated from coffee beans, such as extracted Chlorogenic acid. Accordingly, the presently disclosed whole green coffee bean products and methods of use provide other unexpectedly superior effects in addition to increased concentration and focus, including but not limited to: improved cardiovascular health; increased resistance to cancer and other diseases; and rapid and sustained weight loss.

Improving Concentration and Focus in Humans Using Whole Green Coffee Powder:

Whole Green Coffee Powder, or "WGCP," in accordance with the principles of the invention, in moderate doses may improve executive functioning for sustained attention and working memory without effecting response inhibition. This method of consuming WGCP may improve focus and concentration humans.

Whole green coffee powder (WGCP) is a fibrous, naturally occurring endogenous substance and is a nonesterified solid source of caffeine. It is processed directly from the whole green coffee bean and contains chlorogenic acid in its natural form. It is distinct from green coffee extract because it is made from the whole bean in a specified process (current patent pending), delivers a solid (not from extract) form of caffeine in capsules, and is sold commercially as GoBean®. The presence of naturally occurring green coffee bean nutrients is not available in coffee extract, and the granularity of green coffee powder releases caffeine and cholinergic acid in an extended delivery. These unique features may impact attention, arousal, and executive functions in individuals who use it.

This study investigated the effects of commercially available dietary caffeine supplement (WGCP) on the ability of neurotypical individuals (i.e., without diagnosed ADHD) to exercise executive functions associated with sustained attention, spatial working memory, and response inhibition (ie, impulsivity). These assessed executive functions promote cognitive activity in a way similar to academic study.

To measure the effects of WGCP on core executive functions used in standard academic study, we used the ADHD Core Battery of the Cambridge Neuropsychological Test Automated Battery (CANTAB). This battery includes several modules: motor screening (data from this module were not used in analysis as it tests fine motor speed and is an introductory exercise to the test battery); rapid visual information processing (RVP, sustained attention); stop signal task (SST, response inhibition); and spatial working memory (SWM, working memory). We also investigated the qualitative effects of WGCP via participant self-report. While tests used to study ADHD and treatments thereof, their use here is not intended to suggest that WGCP as discussed herein is used to treat ADHD. Rather use of these test procedures is used only to verify the efficacy of WGCP to improve general focus and concentration among humans generally.

Fourteen adults aged 18-25 years, acted as their own controls in three treatment conditions within a seven-session withdrawal design. Participants completed the Cambridge Neuropsychological Test Automated Battery for attention-deficit/hyperactivity disorder (ADHD) at each session. The Side Effects Behavior Monitoring Scale (SEBMS), used to assess stimulant effects in individuals with ADHD, was a secondary outcome measure to assess adverse events associated with caffeine intake delivered by capsule. Self-report of qualitative effects was collected.

Results indicated that moderate doses of WGCP significantly improved sustained attention (vs placebo and low dose) and working memory (vs low dose only) but had no effect on response inhibition. Low doses of WGCP showed decreased sustained attention. Fifty percent of subjects reported positive subjective improvement in well-being. No side effects were reported.

The study explored the following primary research questions:

1. What are the effects of WGCP compared with placebo on sustained attention, response inhibition, and spatial working memory?

2. How do subjects qualitatively describe the effects of WGCP on affective presentation in daily activity?

Method

This study used a small N approach to acquire preliminary information on the effects of WGCP. Small N studies are limited in controlling variability, but repeated measures allow them to be useful especially when studying novel treatments. The power of well-designed repeated measures designs is evident in that with 10 participants, receiving only five measurements across the study, power to detect significant differences within subjects across conditions is quite good (power=0.89 using Cohen's f) when a large effect size (f=0.40; ~d=0.80), moderate test-retest reliability (correlation) between repeated measurements (r=0.60), and a typical Type 1 error rate (0.05) are assumed. A large effect size is entirely reasonable to expect in repeated measures designs and the test-retest correlation is likely to actually be larger, possibly as high as the reported test-retest reliability of the test ($\square$0.80) which would drive power even higher ($\square$0.99). Readers interested in statistical analyses for this study may contact the first author for syntax.

Assumptions of study design. Referenced in previous studies with caffeine delivery, the following documented characteristics of caffeine are assumed for the use of WGCP in this study: (1) washout of WGCP effect will occur rapidly similar to caffeine washout in other delivery systems (ie, over the period of several hours); (2) dosing may be abruptly terminated without adverse side effects; (3) WGCP effects at moderate dose are not dependent on gradual increase from low dose, that is, subjects do not need gradual exposure to caffeine from low dose (in all cases, nevertheless, low dose preceded moderate dose); (4) onset of WGCP effect is established within one hour as is typical of caffeine products used in previous studies. Essentially, given no evidence to the contrary, WGCP will produce caffeine effects similar to other delivery systems.

Procedures.

We used a repeated measures withdrawal of treatment design to examine the differential effects of a commercially available dietary supplement (GoBean®) and placebo in neurotypical college-age adults, aged 18 to 25 years. The design removes variability through improved experimental control of treatment conditions. A withdrawal of treatment design allowed multiple observations of a small number of subjects (compared to randomized clinical trial designs that use few observations of many subjects). The design alternated treatment and no-treatment conditions across days within single subjects to provide sensitive examination of dose effects. Collection of time-series data permitted the assessment of ongoing treatment-related changes across each presentation of the dependent variable.

The trial is initiated in the baseline (BL) phase of an experimental manipulation of variables. The placebo (A) phase is alternated with the experimental phases. In this study, B1 was the first dose of the active compound (ie, WGCP), and B2 the second dose of the active compound. The Phase A is an intermediary phase between BL and active compound (B1 and B2) and controls for an expectancy of improvement associated with mere ingestion of a capsule as part of a trial (ie, placebo effect). We maintained the rule central to experimental manipulation of variables—only one variable was changed at a time. This allowed for opportunity to distinguish between expectancy (ie, placebo) and WGCP effects.

After a verbal inquiry to confirm overnight caffeine abstinence, subjects received three identical capsules at each session with varying number of capsules containing WGCP. Each capsule contained placebo or 444.8 mg WGCP proprietary blend (55 mg caffeine as per GoBean® package label). Capsules were administered orally once each day in the presence of the study coordinator and one hour prior to CANTAB. Supplements were supplied in labeled plastic containers with study and subject randomization information (ie, study session number and subject coded identification), and sponsor on the label. In Phase A (placebo), all the three capsules contained an inert substance (ie, corn starch); in Phase B1, subjects received one placebo capsule and two WGCP capsules (889.6 mg); and in Phase B2, subjects received three capsules each with the same equivalent dose of WGCP (1334.4 mg). Package label instructions for using WGCP include a three-capsule dose. The study ran seven months (February-August 2013). Study visits were separated by at least one day with an average 3.66 days between each dose administration, and a range of 1-15 days. Six subjects were administered GoBean and the CANTAB before noon, and eight subjects were administered GoBean and the CANTAB between noon and 6:00 pm.

The order of the dose was not randomized since the concern was not if dose improves performance but only whether WGCP improved performance. To varying degrees across subjects, this also permitted us to detect residual effects of withdrawal. Because the safety of subjects is always paramount and despite the assumption that WGCP does not require gradual introduction, we moved from low to moderate dose to ensure that the subjects did not start with a dose to which they may be overly sensitive.

Because the order of presentation of treatment was defined a priori, placebo was counterbalanced across two orders of treatment to maintain the double-blind requirement; experimenters were unaware of the order of treatments. The counterbalanced treatment orders are indicated below:

I. BL-A-B1-A-B2-A-B2
II. BL-B1-A-B2-A-B2-A

We assessed for subjects' medications, recreational drugs, or caffeine consumed through diet or other supplements prior to each administration and relied on subjects' accurate representation through verbal query.

The study focused on acute administration of WGCP, that is, subjects were provided doses of caffeine within a short period. This was practiced because similar studies with chronic caffeine use showed diminished sustained attention and working memory compared to those who abruptly terminated chronic caffeine use.

Eligible subjects were randomly assigned to orders I and II; eight subjects received presentation I and six subjects received presentation II. Each subject arrived at the clinic at the same time in each experimental phase and the assigned times did not differ across placebo and active WGCP days. As an example, if Subject 1 arrived for her BL visit at 8 am, she came to subsequent WGCP active and placebo visits at 8 am. After arrival, subjects were given the randomized dose of WGCP and/or placebo. In one hour, subjects were presented the CANTAB which took approximately 30 minutes to complete and was administered at the same time of day, replicating BL conditions. The CANTAB was presented in a quiet, moderately lit room located in the library of a local university campus or in a similar room in a hospital setting; each subject completed the CANTAB in the same room in which it was initiated. Sessions were separated by at least 1 day to completely eliminate carryover effects as WGCP has duration of action of 4-6 hours (as per package label). After CANTAB administration, subjects verbally completed the Side Effects Behavior Monitoring Scale (SEBMS) with the study coordinator.

Statistical analyses of CANTAB subtests. Sustained attention was measured using the discriminability parameter of the Rapid Visual Processing subtest. Response inhibition was measured using stop signal reaction time from the Stop Signal subtest. Spatial working memory was measured using total errors from the Spatial Working Memory subtest. For each dependent variable, a generalized estimating equations (GEE) model was computed with Treatment (placebo, low dose, and moderate dose) as fixed-factor predictors and the dependent variable as the response variable. GEE is advantageous in that it flexibly accounts for repeated measurements with each participant permitting missing data and explicitly modeling relationships between repeated measures conditions. Alternative covariance structures were examined. Results are based on autoregressive structure. GEE analysis assumed a Poisson distribution with log-linear link for ordinal/count data and a normal distribution with linear link for continuous data. The analyses estimate treatment condition effects using all available conditions. They are not technically averaged but rather using GEE models with all available data, the estimate is generated based on data from each instance of each treatment condition. Preliminary analyses examined order effects. However, there were no significant main effects or interactions with order. Therefore, results are presented without order included as an independent variable. Further-more, given that the low- and moderate-dose conditions were in opposite directions relative to placebo, it is highly unlikely that any order effects influence the pattern of results.

Measures

The CANTAB ADHD Battery was the primary outcome measure. It has been demonstrated to detect neuropsychological effects with selectivity and sensitivity, allows ready interpretation of the effects, and it has a variety of applications in psychology, neuropsychology, and medicine.

The Motor Screening Task is administered at the beginning of the CANTAB and assesses whether a subject can respond to the requirements of the other tasks in the battery; it confirms appropriate visual, movement, and comprehension abilities. Rapid Visual Processing of Information (RVP) is a test of sustained attention and is similar to the commonly used Continuous Performance Test; it is a sensitive measure of general cognitive performance. The Stop Signal Task (SST) is a common assessment task used to assess response inhibition; it estimates an individual's reaction time and gives a measure of how well an individual can inhibit responses and resist the tendency to respond automatically. Spatial Working Memory (SWM) is a test of the participant's ability to use working memory by retaining spatial information, remembering items, and manipulated them in space; this test measures global executive dysfunction.

The CANTAB subtests were administered once in each session. Published studies demonstrated that parallel versions of the CANTAB allow repeated measures and that the CANTAB shows very small practice effects over repeated measures.

Qualitative descriptions and adverse events were assessed in each session. Side effects were assessed using the SEBMS adverse events checklist. The SEBMS uses the Clinical Global Impressions-Severity (CGI-S) anchored scale (1=normal, 2=borderline, 3=mild, 4=moderate, 5=marked, 6=severe, and 7=most extreme).22,23 Subjects completed the SEBMS at the end of each session to track change in behavior. All ratings were based on participants' subjective experience of the 1.5-hour period and on subjective reports between sessions. An adverse event was defined as any untoward medical or physical occurrence in a subject administered WGCP during the course of the study. Participants were probed as to the presence of side effects including heart function anomalies.

The ADHD Rating Scale (ADHD-RS) is an 18-item scale used to rule out symptomatic attentional difficulties. It was administered at BL coinciding with assessment of working memory and response inhibition as measured by the CAN¬TAB. It was used to screen for the presence of ADHD. Scores over 32 are generally considered symptomatic threshold.

Drug screening was conducted by inviting the participants to give verbal self-report of use.

Subjects

Inclusion criteria. To be eligible for inclusion, participants met criteria at initial screening and BL, in which (a) a written consent was signed by the participant; (b) the participant was aged 18-25 years; (c) females of childbearing age had a negative response to a verbal inquiry for pregnancy and were not at risk for becoming pregnant; (d) participants completed an ADHD rating scale; (e) participants had a minimum level of intellectual functioning (determined by the investigator, all participants were or had been enrolled in college courses); (f) symptom criteria for a comorbid mental health condition that could affect safety or tolerability of medication, or interfere with the participant's participation in the study were not in evidence; (g) blood pressure measurements were within the 95th percentile for age and gender at screening; and (h) participants were able to comply with the requirements of the study protocol.

Exclusion criteria. At screening or BL, eligibility was declined if the participant (a) had a current, controlled, or uncontrolled comorbid psychiatric diagnosis with significant symptoms, that, in the opinion of the study investigator, contraindicated treatment, or assessment; (b) was suspected of substance abuse or dependence disorder within the past 12 months in accordance with DSM-IV-TR criteria; (c) admitted to the use of prescription or illegal substance; (d) had a history of seizures during the last two years, a severe tic disorder, and a current diagnosis or family history of Tourette's syndrome; (e) had a conduct disorder; (f) had taken an investigational product within 30 days prior to screening, or participated in any other research study during the trial; (g) had clinically significant blood pressure abnormalities at BL; (h) had a known history of structural cardiac abnormality; (i) had a concurrent chronic or acute medical illness that would prohibit the participant from completing the study or would not be in the best interest of the participant; (j) taking any medications that are excluded, have other central nervous system (CNS) dysfunction, or effect performance, such as sedating antihistamines and decongestant sympathomimetics (bronchodilators were not exclusionary); and (k) the female subject was pregnant or lactating.

Subject confidentiality and consent. Subjects were interviewed by the study investigator or study coordinator. Subjects signed the consent form during the interview period and consents were obtained at least one week prior to the start of the study period. The hospital Institutional Review Board (IRB) approved the study protocol and informed consent procedures.

Results

A total of 16 adults not diagnosed with ADHD or other psychiatric conditions were screened for participation; 14 enrolled in the study (see Table 1). This study population was useful because of participants' ongoing engagement with academic tasks. Academic studies require sufficient working memory and the ability to delay a response to competing activities (eg, participating with friends) to complete required academic work.

TABLE 1

Subject Demographics

|  | Order 1 (Placebo First) | Order 2 (Placebo 2$^{nd}$) | P-Value |
|---|---|---|---|
| n | 8 | 6 |  |
| Male (n, %) | 2 (25.0%) | 2 (33.3%) | .594 |
| White non-Hispanic (n) | 8 | 6 |  |
| Age (M, SD) | 21.25 (1.49) | 21.83 (1.94) | .662 |

Note:
non-parametric statistics ((Mann-Whitney U and Fisher's exact test) were computed.

The study generated information on the effects of WGCP on: a) sustained attention (RVP), b) response inhibition (SST), c) spatial working memory (SWM), and d) qualitative descriptions of the effects of WGCP among young adults.

Results indicated a significant overall treatment effect for sustained attention (Rapid Visual Processing–total misses) ($c2(2)$=58.62, P $\square$ 0.001). Low-dose WGCP resulted in significantly worse sustained attention than placebo in significantly better sustained attention than placebo ($c2(1)$=5.22, P=0.022). Significant differences were also noted in working memory ($c2(1)$=26.36, P=0.001). Spatial working memory errors were highest in the low-dose WGCP and lowest in the moderate-dose WGCP. Placebo fell in-between these values but pairwise comparisons were not statistically significant (low dose vs placebo $c2(1)$=1.11, P=0.293 and moderate dose vs placebo $c2(1)$=2.15, P=0.142). No significant differences were observed for response inhibition (impulsivity) (overall P=0.0579; see Table 2).

TABLE 2

Treatment effects on CANTAB

| PARAMETER | CANTAB TASK | $\chi2$-VALUE | P-VALUE | PLACEBO MEAN (SE) | WGCP LOW DOSE MEAN (SE) | WGCP MODERATE DOSE MEAN (SE) | WGCP LOW DOSE VS. PLACEBO (d) | WGCP MODERATE DOSE VS. PLACEBO (d) |
|---|---|---|---|---|---|---|---|---|
| Sustained attention | RVP | 58.62 | p $\square$ .001 | 3.24 (0.58) | 4.43 (0.69) | 2.46 (0.49) | .29 | −.23 |
| Response inhibition | SST | 1.09 | p = .579 | 142.8 (6.5) | 145.3 (6.0) | 139.0 (5.0) | −.06 | .10 |
| Spatial working memory | SWM | 26.36 | p $\square$ .001 | 4.62 (1.39) | 6.00 (1.66) | 3.86 (1.38) | .14 | .09 |

Abbreviations:
RVP, Rapid Visual Information Processing - Total missed targets (lower scores indicate better performance);
SST, Stop Signal Task - reaction time last half of task (lower scores indicate faster performance);
SWM, Spatial Working Memory Task - total errors (lower scores indicate better performance).

The mean ADHD rating scale score was 26.4 and nonsymptomatic for ADHD. Subjects did not differ on measures of attention dysfunction (see Table 3).

TABLE 3

ADHD rating scale measures of attention dysfunction.

| | MEAN SCORE | | | | |
|---|---|---|---|---|---|
| TARGET SYMPTOMS | BASELINE | PLACEBO | WGCP LOW DOSE | WGCP MODERATE DOSE | $X^2$ (p) |
| Overactivity; motor restlessness | 1.29 | 1.36 | 1.34 | 1.34 | 2.89 (.409) |
| Impulsiveness; acting without thinking | 1.33 | 1.26 | 1.27 | 1.26 | 8.58 (.035) |
| Distractibility; sustaining attention to tasks | 1.57 | 1.54 | 1.44 | 1.60 | 3.70 (.296) |
| Task completion; finishing tasks | 1.17 | 1.11 | 1.09 | 1.13 | 3.00 (.392) |
| Being on time/Accepting limits | 1.14 | 1.14 | 1.14 | 1.14 | — |
| Following Instructions | 1.13 | 1 | 1 | 1 | — |
| Frustration tolerance; appropriately expresses frustration | 1.21 | 1.21 | 1.21 | 1.21 | — |
| Ability to calm self when excited | 1.43 | 1.41 | 1.63 | 1.36 | 2.39 (.495) |
| Non-family/Peer relations | 1.07 | 1.07 | 1.07 | 1.07 | — |
| Family/Close relations | 1 | 1 | 1 | 1 | — |

Notes:
GEE analysis assuming poisson distribution with log-linear link for ordinal/count data. Wald c2 degrees of freedom equals 3. In many cases, the counts were of extremely low variability (almost entirely scores of 1). Therefore, test statistics could not be computed or should be seen only as descriptive of the general pattern.

Qualitative results. At the end of each session, participants gave subjective accounts of their experience from the time they ingested capsules until the completion of the CANTAB (approximately one and a half hours). In addition, they described reactions from the previous administration of WGCP. The SEBMS probed whether any of the 20 specific side effect reactions to stimulant medication were present. Participants showed no adverse events (Table 4). When probed whether they discerned receiving an active dose or placebo, seven participants were unable to identify whether they received active ingredient or placebo; seven participants accurately discerned that they had received WGCP moderate dose but not the low dose.

Participants reported qualitative reactions to the moderate dose that are best defined in three areas: (1) increased efficiency on tasks, (2) enhanced ability to stay on task, and (3) a feeling of well-being. For example, Participant 14 stated that she felt "extra focused on the work I did in the morning." Participant 10, a college student, stated that she "felt really good and focused even though I have a lot to do today." Participant 8 reported, "I got more done in an hour today compared to yesterday." Others reported "feeling good" and the absence of feelings of malaise or intrusive emotions.

Other qualitative reports show that acute exposure to WGCP, as administered in this study, resulted in increased alertness, improved concentration, decreased fatigue, and significantly increased feelings of contentedness and satisfaction.

Side effects are summarized in Table 4. No significant side effects are reported. Side effect ratings on the CGI-S are all rated as normal or not at all present.

Discussion

This study confirmed effects of improved sustained attention and, to a lesser extent, spatial working memory with WGCP intake. Sustained attention showed improvement with moderate-dose WGCP, including separation from placebo and low-dose WGCP. The results for working memory were similar in pattern but quantitatively weaker, with moderate-dose WGCP showing improved working memory relative to low dose but not versus placebo. Results indicated a negative effect on sustained attention and working memory for low-dose WGCP (two capsules) contrasted with the strong positive effect for moderate-dose WGCP (three capsules). The positive effect of moderate-dose WCGP on sustained attention was modest in size (d=−0.23). Although not dramatic, this effect may be clinically meaningful and may be noticeable to individuals when working in contexts that require substantial sustained attention. The inhibitory effect at low dose is difficult to explain. At a low dose, WGCB may inhibit fatigue but it may not deliver enough caffeine to produce the cognitive effects that moderate doses do. If low dose was simply a non-effect, then placebo and low dose should be similar. They were not similar, however; low dose inhibited response. The inhibitory function of low dose may be evidence of a side effect, such as minor agitation, that occurs at smaller doses of WGCP. Individual variance of response may also explain these effects.

TABLE 4

Side effects behavior monitoring scale.

| SIDE EFFECT | BASE LINE | PLACEBO | WGCP LOW DOSE | WGCP MODERATE DOSE | $X^2$ (P) |
|---|---|---|---|---|---|
| Insomnia or trouble sleeping | 1.43 | 1 | 1.14 | 1 | 6.00 (.112) |
| Nightmares | 1.07 | 1 | 1 | 1 | 1.08 (.299) |
| Stares a lot or daydreams | 1.43 | 1.21 | 1.21 | 1.14 | 5.68 (.128) |
| Talks less with others | 1.21 | 1.02 | 1.07 | 1 | 3.64 (.303) |
| Uninterested in others | 1.14 | 1.02 | 1 | 1 | 4.78 (.187) |
| Decreased appetite | 1.29 | 1.05 | 1 | 1 | 2.34 (.504) |
| Irritable | 1.43 | 1.05 | 1.14 | 1.04 | 7.10 (.069) |
| Stomachaches | 1.29 | 1.02 | 1.21 | 1.04 | 3.45 (.328) |
| Headaches | 1.57 | 1.17 | 1.29 | 1.14 | 6.87 (.076) |
| Drowsiness | 1.71 | 1.69 | 1.57 | 1.36 | 7.91 (.048) |
| Sad/Unhappy | 1.21 | 1.02 | 1 | 1.07 | 3.52 (.318) |
| Prone to crying/Easily upset | 1.21 | 1 | 1 | 1 | 2.07 (.151) |
| Anxious/Worried | 1.43 | 1.02 | 1.07 | 1.11 | 5.17 (.160) |
| Perseveration (verbal or behavioral) | 1.14 | 1 | 1 | 1 | 2.33 (.127) |
| Bites/Picks skin or fingernails | 1.36 | 1.02 | 1.07 | 1 | 7.77 (.051) |
| Euphoric/Unusually happy/Mania | 1.21 | 1 | 1 | 1.07 | 3.82 (.148) |
| Dizziness | 1.14 | 1.10 | 1.14 | 1.14 | 2.74 (.433) |
| Tics or nervous movements | 1.07 | 1.07 | 1.07 | 1 | 2.67 (.446) |
| Overfocused (tunes others out) | 1.21 | 1.19 | 1.21 | 1.18 | 0.04 (.998) |
| Hallucinosis | 1 | 1 | 1 | 1 | — |
| Flat affect/Emotional blunting | 1 | 1.02 | 1 | 1 | 1.08 (.299) |
| Dry mouth | 1 | 1 | 1.07 | 1.04 | 1.08 (.299) |
| Numbness or tingling in extremities | 1.14 | 1.05 | 1 | 1 | 2.67 (.446) |

Notes:
Wald c2 degrees of freedom equals 3. In many cases, the counts were of extremely low variability (almost entirely scores of 1). Therefore, test statistics could not be computed or should be seen only as descriptive of the general pattern. 1 = normal, 2 = borderline, 3 = mild, 4 = moderate, 5 = marked, 6 = severe, and 7 = most extreme.

WGCP at a moderate dose tended to be associated with a qualitatively positive affective response. In interview, subjects reported a sense of well-being and an ability to initiate tasks more easily. For example, use of WGCP decreased ratings of sleepy, tired, drowsy, "half awake", lazy, and sluggish. Subjects reported that they experienced an overall sense of contentedness and that they felt more at ease, relaxed, and satisfied. The substance induced more reportedly energetic feelings as well as heightened friendliness and sociability. In addition, evidence from previous studies14 and common knowledge indicate a deleterious effect (e.g., jitteriness or nervousness) of chronic caffeine ingestion. However, subjects in this study did not report these effects with WGCP. Additionally, inquiries regarding heart palpitations, rapid rate, or other cardiac function anomalies were not reported in probed interview.

It is an interesting finding that moderate-dose WGCP improved spatial working memory relative to low dose. Working memory is a complex function that involves the ability to manipulate and control information such that the information is both symbolically stored and processed in verbal and spatial forms. Neurologically, the information processed in working memory is stored throughout the brain depending on the nature of the eliciting information.25 Caffeine effects, functionally altering the adenosine receptors, may impact the wide variety of neural pathways associated with working memory and may require higher WGCP concentration.

The finding that WGCP did not affect response inhibition is expected. Inhibitive functions are typically considered to be prefrontal, neurological events. Response inhibition is the ability to keep interfering information away from focused attention. It, too, is complex and may be outside the effects of neural pathways associated with caffeine effects as delivered by WGCP.

The nature and mode of delivery of caffeine may influence its effect on executive performance. According to the packaging label of GoBean®, the delivery of caffeine using WGCP provides the "natural caffeine that is deep within the fiber of the bean." Caffeine extracts rather than "natural caffeine" are typically used in commercially sold liquid products. The study did not compare WGCP with other caffeine delivery systems. It is possible that the effects on sustained attention and the reported positive qualitative effects may be a function of both caffeine and the nutrients that are not available in extracts. In addition, effects of WGCP may also be due to the mode of ingestion. The method of delivery—taking a capsule vs drinking a liquid—may represent a distinct difference in caffeine effects.24 Although the features unique to WGCP are interesting, further study is required as this investigation does not provide information on the addition of nutrients in caffeine or on the delivery provided by WGCP; further investigation is required.

Research is certainly required to fully appreciate the different effects on attention and behavior associated with WGCP. Many studies of the effects of caffeine were conducted more than a decade ago, however, and these relied on extract rather than on caffeine occurring in its natural state. Given the variety of availability of caffeine products from diet supplements to energy drinks, study of new delivery systems of the raw bean is warranted especially as this relates to adverse events.

A consideration of the study is the carryover of WGCP effects from one phase of the manipulation to the other. This problem was handled in the counterbalanced repeated measures design of the study. In future studies, however, length of phases may be varied to determine WGCP latency effects (ie, onset of action of WGCP), and residual effects (ie, persisting WGCP effects during placebo phase) after active WGCP is terminated. Both latency and residual effects must be investigated to engage larger N trials to ensure safety of subjects and to determine timeliness of active WGCP exposure.

An interesting finding is that seven subjects (50%) were unable to discern between placebo and active WGCP, and the remaining subjects discerned only the moderate WGCP dose but not the low dose. Many factors impact whether a person recognizes changes in personal physiology; factors such as reaction sensitivity, ability to self-observe bodily changes, the opportunity to note changes (e.g., a busy day full of attention occupying activity impairs self-monitoring vs a relatively calm, predictable day that allows it) and the same may explain this phenomenon.

The above steps are set forth to illustrate general concepts. Numerous other steps, and combinations and permutations thereof, are contemplated, and are inherently and necessarily disclosed to persons of ordinary skill in the art by the foregoing description.

Although exemplary embodiments and applications of the invention have been described herein, there is no intention that the invention be limited to these exemplary embodiments and applications or to the manner in which the exemplary embodiments and applications operate or are described herein. Indeed, many variations and modifications to the exemplary embodiments are possible as long as the resulting methods and products fall within the scope of one of the following claims or its equivalent.

Use Treating or Preventing Diabetes:

WGCP has potent antioxidative properties and its consumption prevents or slows the development of NIDDM. The polyphenol Chlorogenic Acid (CGA) has demonstrated potential for anti-diabetic activity. CGA regulates glucose by stimulating uptake in adipocytes. A recent study demonstrated a 6.9 percent decrease in the absorption of glucose over 120 minutes following the administration of CGA enriched Green Coffee powder. CGA has demonstrated effects similar to rosiglitazone in clinical trials. Chlorogenic Acid is the main active phenolic in WGCP accounting for 42.2 percent of all phenolics. The identified chlorogenic acids in WGCP include: dicaffeoylquinic, caffeoyl, feruloyl, and p-coumaroyl quinic acids. Several other phenolics contribute to the active component of WCGP including: Catechin, Isochlorogenic acids, Ferulic Acid, Protocatechuic Acid, and Rutin. The complete breakdown is shown in table 1.

TABLE 1

Polyphenol Composition of WGCP

| Polyphenol | Percentage* |
|---|---|
| Chlorogenic Acids | 42.2 |
| Epicatechin | 21.6 |
| Catechin | 2.2 |
| Isochlorogenic Acids | 29.4 |
| Ferulic Acid | 1.0 |
| Protocatechuic Acid | 1.6 |
| Rutin | 2.1 |

*rounded to one decimal

Without being bound by theory, the inventor believes that the combination of CGAs in WGCP interact synergistically and the combined constituent polyphenols exhibit increased effectiveness by inhibiting glucose uptake via sodium-dependent transporter cells in the intestine and by improving insulin-stimulated glucose uptake. WGCP was tested to measure its efficacy in treating and/or preventing diabetes, as explained below:

Methods:

Ten ambulatory study participants with elevated Hemoglobin A1c (HbA1c) were selected nonrandomly and studied over the course of 12 weeks. Seven were men and three were females. Before study initiation every participant had a venous-blood sample to measure Hemoglobin A1c (HbA1c) levels. Each participant received 90 days of Whole Green Coffee Powder commercially prepared in single serving ready to drink bottles. Each bottle contained a liquid suspension with 4 grams of WGCP per serving. The participants were directed to use one serving every morning for 12 weeks. The test subjects were instructed to maintain their normal daily dietary and exercise habits. The participants were also instructed to avoid adding any additional over-the-counter health products to their current regimen. All patients signed written consents prior to the start of the study.

The following criteria were used for study selection: 1) Subjects had a recent lab test by a referring provider demonstrating an elevated HbA1c level; 2) Subjects had a repeat HbA1c that met the American Diabetes Association (ADA) criteria to diagnose diabetes or prediabetes; 3) Subjects met the required Prediabetic ranges A1C 5.7-6.4% (39-46 mmol/mol), Diabetic A1C≥6.5 (48 mmol/mol); 4) Subjects were not currently taking medication for the management of diabetes.

TABLE 2

Clinical characteristics of patients

| Patient | Sex | Age | Pre A1C | Post A1C |
|---|---|---|---|---|
| 1 | M | 48 | 6.4 | 5.6 |
| 2 | M | 54 | 6.9 | 5.9 |
| 3 | F | 48 | 7.5 | 6.9 |
| 4 | M | 37 | 7.4 | 6.3 |
| 5 | M | 70 | 8.4 | 7.0 |
| 6 | M | 38 | 8.5 | 7.2 |
| 7 | F | 45 | 6.5 | 5.6 |

Results:

The study characteristics are shown in Table 2. The initial sample size was 10 subjects. Two subjects did not complete the study. Of the eight subjects that completed the study, seven were used in the analysis. The remaining subject was removed from the analysis after a follow-up autoantibodies test confirmed a diagnosis of diabetes type 1. Mean age was 48.6 years.

HbA1c levels were converted to Estimated Average Glucose Levels eAG to facilitate analysis. Table 3. Average serum glucose concentration was 164.9 mg/dl at the start of the study. Average serum glucose concentrations decremented to 135.7 mg/dl after 90 days of WGCP administration.

When baseline estimated average serum-glucose levels are compared against the post treatment levels, a decrease of 17.7 percent was observed.

TABLE 3

HbA1c to eAG conversion in mg/dl

| Patient | Pre eAG | Post eAG |
|---|---|---|
| 1 | 137 | 114 |
| 2 | 151 | 123 |
| 3 | 169 | 151 |
| 4 | 166 | 134 |
| 5 | 194 | 154 |
| 6 | 197 | 160 |
| 7 | 140 | 114 |

The hypoglycemic properties observed may represent a nonpharmacological adjunctive to managing elevated glucose levels. The decrement observed was 29.2 mg/dl in estimated average daily glucose levels. This represents a clinically significant finding and demonstrates that WGCP may be used to reduce glucose levels over extended time period of a least three months.

Use Treating or Preventing Obesity:

A 12 week randomized double blind placebo controlled prospective clinical study was used to assess the efficacy, safety and tolerability of a WGCP dietary supplement weight loss formulation, along with diet and exercise, in reducing body weight and hunger and increasing satiety, mood and energy, when compared to placebo and diet and exercise alone. Efficacy was assessed by measuring body weight, impedance, anthropometrics and satiety, and safety by measuring resting heart rate, blood pressure, and monitoring side effects through subjective questionnaires.

Methods

Consenting eligible male and female subjects, meeting the inclusion/exclusion criteria, were required to visit the study site three times for screening, Week 6 and week 12 activities. There were a total of seventy four subjects enrolled, randomly assigned to two groups of thirty eight subjects each, corresponding to placebo and active. Study medication was provided as indicated below under "product use".

During the screening visit to the study site, Informed Consent and Bill of Rights forms were signed by subjects after a thorough review with the PI or CRC. Subjects must have been able to read, understand, accept, and sign the Informed Consent form. Subjects completed a screening health questionnaire and underwent a brief physical examination by the PI. A urine pregnancy test was carried out for female patients just prior to the start of the study.

Subjects selected to participate in the study were provided with instructions on completing the various forms related to the study endpoints and study procedures, and were instructed to check with the Investigators or Clinical Research Coordinator (CRC) if they had any questions.

All groups were asked to exercise four times a week by walking briskly for 30 minutes, while being able to carry out a conversation or periodically recite a text of their choice. Subjects were also asked to record their exercise dates and time via diary for each walk.

Subjects provided a 3-day log of meals and snacks, which they brought to the site on the initial visit date. A registered dietician (RD) evaluated subject diets based on these logs and provided appropriate recommendations for food to eat during the study in the form of possible menus. These data were used only for informational purposes. Side effects were monitored using a questionnaire, vitals and EKG. Study activities are shown in Table 1—Study Schedule of Events.

STUDY ENDPOINTS. The following endpoints of each event were evaluated at various intervals as shown in Table 1—Study Schedule of Events, shown in FIG. 7.

Efficacy Measurements:
BMI measurements (0, 6 and 12 weeks)
Body weight measurements (0, 6 and 12 weeks)
Body fat calipers at abdomen and impedance % body fat via BIA scale
Anthropometrics—height, weight, hip and waist circumference (0, 6 and 12 weeks)
Satiety VAS scales—(0, 6 and 12 weeks-administered during the study an hour after breakfast, lunch and dinner)
Energy VAS scales—(0, 6 and 12 weeks-administered an hour after taking the Product)

Safety Measurements:
Subjective side effect questionnaire (6 and 12 Weeks)
Vitals: HR, BP (0, 6 and 12 weeks)
Physical exam
Medical history (screening)
Comprehensive metabolic panel (6 and 12 weeks)
Electrocardiogram (EKG) (week 0)

Subjects and Subject Selection Criteria

Subjects were recruited from the clinical private practice setting, online ads, local newspaper ads, and word of mouth. Eligibility was assessed through telephone pre-screening.

Inclusion Criteria:
Male and female volunteers
Ages between 18 and 65 years
In general good health
BMI=27-37
Agree to exercise for 30 minutes by walking 4 times a week
Agree to diet maintenance per RD evaluation (See study design for details)
Must be able to read, understand, accept, and sign the informed consent document.

Exclusion Criteria. Subjects who met any of the following conditions or medical history were excluded:

If they fail the physical exam by the Principal Investigator (PI)

If they have any metabolic disorder including known electrolyte abnormalities

If they have heart disease, arrhythmias, diabetes, thyroid disease, or hypogonadism, a history of hypertension, hepatorenal, musculoskeletal, autoimmune, or neurologic disease, or any other condition deemed exclusionary by the PI If they are taking thyroid, hyperlipidemic, hypoglycemic, anti-hypertensive, anti-depressant, or androgenic medications or any other medications deemed exclusionary by the PI If they have taken nutritional supplements that may affect muscle mass (e.g., creatine, HMB), fat loss (e.g., ephedra) or anabolic/catabolic hormone levels (androstenedione, DHEA, etc.) within one month prior to the start of the study Using any fat loss supplements, special diet program, steroids, and other athletic performance enhancing supplements or drugs.

If they are currently using any medication that conflict with the product ingredients Pregnant or lactating women or women not taking medically approved birth control.

Women planning to become pregnant within 30 days of the start of the study or during the study period
Habitual smoking
More than 2 alcoholic drinks per day average 14 per week STUDY PRODUCTS. The following was the composition of the test products for all oral formulations and spray:
Active capsule, WGCP supplement (per capsule)
a. Active ingredients:
Caffeine: 15 mg
Whole Green Coffee Powder: 1159 mg
Chlorogenic Acid: 42 mg
b. Inactive Ingredients:
Gelatin,
Rice Bran
Chlorophyll
Placebo capsule:
a. Active ingredients: None
b. Inactive Ingredients:
Rice Starch capsules
Chlorophyll (colorant)

MANUFACTURERS. Active and Placebo were both manufactured and supplied by GoBean Green Coffee Products, LLC, Scottsdale, Ariz.

PRODUCT ADMINISTRATION. Subjects were instructed to take 3 capsules 30 minutes prior to a major meal (breakfast or lunch, or dinner), twice daily, for 12 weeks. (6 capsules total per day)

STATISTICAL ANALYSIS. A randomized treatment list was generated for assigning each subject to the active or placebo treatment group. For continuous measures, means and standard deviations were calculated for demographic and vitals measures, and medians and interquartile ranges (IQR) were calculated for hunger, satiety, energy and mood VAS scales. Independent samples t-test were used to compare means between treatment groups and Wilcoxon Rank Sum tests were used to compare medians between treatment groups. Chi-Square and Fisher's Exact tests were used for categorical variables. SAS (SAS Institute, Cary N.C.) was used for all analyses and the accepted level of significance was $\alpha=0.05$.

Results

STUDY SUBJECT FLOW. Seventy four subjects were enrolled into the study and randomly assigned into one of two treatment groups, active or placebo, each consisting of thirty eight subjects. FIG. 8 shows Table 2—Study Subject Flow Chart, which summarizes study subject flow information.

DEMOGRAPHICS, BODY MEASUREMENTS AND VITALS. Demographics, body measurements and vital signs for baseline are reported in Table 3A, shown in FIG. 9. At baseline screening, no significant differences were found between treatment groups for age, gender and vital signs (systolic and diastolic pressure and pulse). There were also no significant differences between treatment groups for height, weight, BMI, % fat from BIA scale, waist circumference and body fat caliper measurements. Hip circumference was higher in the active group (p=0.04).

Body measurements and vital signs for Weeks 6 and 12 and changes from baseline are reported in Tables 3B and C, shown in FIGS. 10 and 11, respectively.

Between group comparisons: There were no significant differences between treatment groups at the week 6 follow-up. At 12 weeks, active mean body fat caliper was higher than the placebo (p=0.05), while the body fat caliper change from baseline was not significant between treatment groups (p=0.30).

Within group comparisons: In the active group there was a significant increase in systolic and diastolic blood pressure from baseline at week 6 (p<0.05). In the placebo group, mean changes from baseline at week 6 decreased for weight and pulse and increased for % fat from BIA scale (p<0.05) and at week 12 increased for systolic and diastolic blood pressure (p<0.05).

Hunger and Satiety Vas Scores

Tables 4A, 4B and 4C are shown in FIGS. 12, 13 and 14, respectively. Hunger and Satiety VAS Scores, for Baseline and weeks 6 and 12 respectively, show these scores and changes from baseline. Changes from baseline are the relevant data here because there were significant differences between groups at baseline. At baseline there were significant treatment differences at time B for hunger Q1-Q3 and for satiety Q4 at times A and B. Times A and B refer to the one time daily that subjects chose to fill their VAS forms following their supplement dose—at either breakfast or lunch, or dinner.

Between group comparisons: At week 6, changes from baseline at Time A, for hunger Question 2 (Desire to eat) there was a decrease in the active by comparison to the control group (p<0.005), and trends for a decrease in hunger Question 1 (How hungry), P<0.07 and an increase in hunger Question 3 (How full), p<0.09, both at Time B.

At week 12, changes from baseline, (time B) for hunger Questions 1 & 2 scores were lower than the placebo scores (p=0.01 and 0.03, respectively). For satiety Questions 2

(How full), Time A, there was an increase, P=0.02 (this same question at Time A was also significant for the actual scores on this question, not just change from baseline, P<0.5) and Question 3 (How much can eat), time A, there was a decrease, P<0.05 by comparison to the control group. For Question 4 (Desire to eat), Time A, there was a trend for decrease, P<0.06, by comparison to the control.

Within group comparisons: At week 6 for the active there was a significant decrease from baseline (time B) for hunger Questions 1 and 2 in the active group (p<0.05) and a trend increase (Time B) for hunger for Question 3, p<0.09.

At week 12 for the active there was a decrease for hunger Question 1 (Times A&B), p<0.05, an increase for satiety Question 2 (Time A), P<0.05 and a decrease for satiety Questions 3 and 4 (Time A), P<0.01.

Energy and Mood VAS Scores

Tables 5A, 5b and 5C, are shown in FIGS. 15, 16 and 17, respectively. Energy and Mood VAS Scores, for Baseline and weeks 6 and 12 respectively, show these scores and changes from baseline. At baseline there were no significant treatment differences at Times A or B for any of the questions. Times A and B refer to the one time daily that subjects chose to fill their VAS forms following their supplement dose—at either breakfast or lunch, or dinner.

Between group comparisons: There were no significant differences between treatments for any of the questions at any time of the points for either original or change from baseline scores, P<0.05.

Within group comparisons: In the active group at weeks 6 and 12, energy decreased for Q1 time B (p<0.01), Q2 time A & B (p<0.05) and at week 12 for Q4 times A & B (p<0.05). At week 6 the active group mood increased for Q4 time A (p<0.05) and decreased for Q2 time B (P<0.01). In the placebo group at week 6, energy decreased for Q1 time A (p<0.05) and Q2 time A & B (p<0.01) and mood decreased for Q2 time B (p<0.05). At week 12, in the placebo group energy decreased for Q1 time A (p<0.05), Q2 time B (p<0.05) and mood decreased for Q5 time A (p<0.05). These changes, however, occurred for the most part in both the control and active groups and therefore are unlikely to be attributable to the supplement. They are marked by two or three asterisks (*) in Tables 5A, 5B and 5C shown in FIGS. 15, 16 and 17.

Comprehensive Metabolic Panel

Tables 6A and 6B are shown in FIGS. 18 and 19. Comprehensive Metabolic Panel summarizes the data for the metabolic panel blood chemistry, which was performed at baseline (Table 6A) and week 12 (Table 6B). There were no significant differences between groups for any of the parameters at baseline. The placebo group mean sodium level was lower than the active (p=0.01) at week 12. He values for both groups, however, were within the normal ranges for sodium and therefore this difference is not of clinical significance.

Exercise Compliance

Table 8-Number of Times Exercised, shown in FIG. 20, summarizes the number of times subjects in the two groups exercised per week. There were no significant differences between groups at weeks 6 and 12 or for the total number of times for the entire 12 week length of the study. P<0.5). The information also verifies that subjects complied with the protocol 4 time a week, 30 min walk, requirement for exercise.

DROPOUTS. There were 15 (40.5%) and 16 (43.2%) dropouts in the active and placebo groups, respectively, as shown in FIG. 9, Table 3A-Demographics, Body Measurements and Vitals—Baseline.

Subject Reported Side Effects

Table 9—Subject Reported Side Effects, shown in FIG. 21, summarizes the side effects for each group at weeks 6 and 12. There were no significant differences between groups across side effects or in total number of side effects, both at 6 and 12 weeks, (P>0.05).

DISCUSSION

There were no significant differences between groups in any of the weight, anthropometric or body composition parameters, or energy and mood scores. There were, however, significant differences in favor of the active group for hunger and satiety assessments at 6 and 12 weeks.

These results indicate that either a longer exposure to this supplement preparation or higher doses, or both, will translate into changes in body weight and energy and mood, as well. The study preparation was well tolerated and there were no significant differences between active and control groups across side effects or in their total number.

Whereas, the present invention has been described in relation to the drawings attached hereto, it should be understood that other and further modifications, apart from those shown or suggested herein, may be made within the spirit and scope of this invention. Descriptions of the embodiments shown in the drawings should not be construed as limiting or defining the ordinary and plain meanings of the terms of the claims unless such is explicitly indicated.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

The invention claimed is:

1. A method of preventing diabetes of a user comprising the steps of:
   the user orally ingesting a whole green coffee bean powder in an amount effective to treat the user, the stabilized unroasted whole green coffee bean powder comprising:
   a material derived from whole green coffee beans in their fresh green unroasted state with naturally-occurring levels of phytonutrients, by sterilizing the unroasted whole green coffee beans and grinding the whole green coffee beans to a size capable of passing a 20 mesh screen; and
   at least one stabilizer;
   wherein the material has not been exposed to temperatures above 130 degrees Fahrenheit for more than several seconds; and,
   wherein the moisture content of the stabilized unroasted whole green coffee bean mixture is less than about two percent.

2. A method of preventing diabetes of a user comprising the steps of:
   the user orally ingesting a product comprising a stabilized unroasted whole green coffee bean mixture in an amount effective to treat the user, the stabilized unroasted whole green coffee bean mixture comprising:
   entire whole green coffee beans having been obtained by removal of pulp and skin from coffee berries, sterile, in their fresh green unroasted state with naturally-occurring levels of phytonutrients, ground to pass through a 20 mesh screen; and at least one stabilizer;

wherein the stabilized unroasted whole green coffee bean mixture has not been exposed to temperatures above 130 degrees Fahrenheit for more than several seconds.

3. A method of treating obesity of a user comprising the steps of:

the user orally ingesting a whole green coffee bean powder in an amount effective to treat the user, the stabilized unroasted whole green coffee bean powder comprising:

a material derived from whole green coffee beans in their fresh green unroasted state with naturally-occurring levels of phytonutrients, by sterilizing the unroasted whole green coffee beans and grinding the whole green coffee beans to a size capable of passing a 20 mesh screen; and at least one stabilizer;

wherein the material has not been exposed to temperatures above 130 degrees Fahrenheit for more than several seconds; and, wherein the moisture content of the stabilized unroasted whole green coffee bean mixture is less than about two percent.

\* \* \* \* \*